United States Patent
Yokoi et al.

(10) Patent No.: US 9,192,768 B2
(45) Date of Patent: Nov. 24, 2015

(54) STIMULATION SIGNAL GENERATION DEVICE AND STIMULATION SIGNAL GENERATION METHOD

(75) Inventors: Hiroshi Yokoi, Chofu (JP); Ryu Kato, Chofu (JP); Tatsuhiro Nakamura, Tokyo (JP); Soichiro Morishita, Tokyo (JP); Osamu Yamamura, Yoshida-gun (JP)

(73) Assignees: The University of Electro-Communications, Tokyo (JP); The University of Tokyo, Tokyo (JP); National University Corporation University of Fukui, Fukui-shi (JP)

( * ) Notice: Subject to any disclaimer, the term of this patent is extended or adjusted under 35 U.S.C. 154(b) by 265 days.

(21) Appl. No.: 13/879,118

(22) PCT Filed: Oct. 14, 2011

(86) PCT No.: PCT/JP2011/073703
§ 371 (c)(1),
(2), (4) Date: Apr. 12, 2013

(87) PCT Pub. No.: WO2012/050200
PCT Pub. Date: Apr. 19, 2012

(65) Prior Publication Data
US 2013/0218238 A1    Aug. 22, 2013

(30) Foreign Application Priority Data
Oct. 14, 2010  (JP) ................ 2010-231881

(51) Int. Cl.
A61B 5/103    (2006.01)
A61N 1/36     (2006.01)
(Continued)

(52) U.S. Cl.
CPC .......... *A61N 1/36103* (2013.01); *A61B 5/0482* (2013.01); *A61B 5/0488* (2013.01);
(Continued)

(58) Field of Classification Search
USPC ............................................. 607/48
See application file for complete search history.

(56) References Cited

U.S. PATENT DOCUMENTS

2004/0131998 A1*  7/2004  Marom et al. ............ 434/236
2004/0172097 A1   9/2004  Brodard et al.
(Continued)

FOREIGN PATENT DOCUMENTS

JP    2004-526541 A    9/2004
JP    2007-515200 A    6/2007
(Continued)

OTHER PUBLICATIONS

T.Yan et al: "Functional Electrical Stimulation Improves Motor Recovery of the Lower Extremity and Walking Ability of Subjects With First Acute Stroke: A Randomized Placebo-Contorolled Trial", Stroke, vol. 36, No. 1, Nov. 29, 2004, pp. 80-85.
(Continued)

*Primary Examiner* — Carl H Layno
*Assistant Examiner* — Jon Eric C Morales
(74) *Attorney, Agent, or Firm* — Marvin A. Motsenbocker; Mots Law, PLLC

(57) ABSTRACT

Implementation including a brain activity data acquisition unit configured to acquire data on brain activity of a human body; a generator configured to generate a stimulation signal based on predetermined stimulation parameters or stimulation parameters determined from the data acquired by the brain activity data acquisition unit, the stimulation signal being to be applied, for activity of a specific brain region to be activated in order to move a joint of the human body, to a nerve corresponding to the specific brain region; and an output unit configured to output the stimulation signal generated by the generator.

21 Claims, 19 Drawing Sheets

(51) Int. Cl.
*A61B 5/0482* (2006.01)
*A61B 5/0488* (2006.01)
*A61B 5/11* (2006.01)
*A61B 5/055* (2006.01)
*A61B 5/107* (2006.01)
*A61B 5/00* (2006.01)
*A61H 23/02* (2006.01)
*A61H 3/00* (2006.01)

(52) U.S. Cl.
CPC ............. *A61B 5/055* (2013.01); *A61B 5/1071* (2013.01); *A61B 5/11* (2013.01); *A61N 1/36003* (2013.01); *A61N 1/36014* (2013.01); *A61B 5/4528* (2013.01); *A61H 3/00* (2013.01); *A61H 23/02* (2013.01); *A61H 2201/5002* (2013.01); *A61H 2201/5005* (2013.01); *A61H 2205/06* (2013.01); *A61H 2205/088* (2013.01); *A61H 2205/102* (2013.01); *A61H 2205/12* (2013.01); *A61H 2230/105* (2013.01); *A61N 1/36021* (2013.01)

(56) References Cited

U.S. PATENT DOCUMENTS

| | | |
|---|---|---|
| 2005/0216071 A1 | 9/2005 | Devlin et al. |
| 2006/0195153 A1 | 8/2006 | DiUbaldi et al. |
| 2007/0179534 A1 | 8/2007 | Firlik et al. |
| 2009/0187124 A1 | 7/2009 | Ludlow et al. |
| 2013/0137549 A1* | 5/2013 | Hamada et al. .................. 482/4 |

FOREIGN PATENT DOCUMENTS

| | | |
|---|---|---|
| JP | 2008-67917 A | 3/2008 |
| JP | 2008-544832 A | 12/2008 |
| JP | 2009-512516 A | 3/2009 |
| JP | 2009-525150 A | 7/2009 |
| WO | 00/90008 A1 | 2/2000 |
| WO | 02/087683 A2 | 11/2002 |
| WO | 02/092164 A2 | 11/2002 |
| WO | 2004/100765 A2 | 11/2004 |
| WO | 2006/074029 A2 | 7/2006 |
| WO | 2007/005582 A1 | 1/2007 |
| WO | 2007/047852 A2 | 4/2007 |
| WO | 2007/090046 A1 | 8/2007 |

OTHER PUBLICATIONS

The extended European search report issued on Sep. 29, 2014 in the counterpart European patent application.

ISR issued on Nov. 15, 2011.

Ryu Kato et al., Mutual adaptation among man and machine by using f-MRI analysis, Robotics and Autonomous Systems, vol. 57, p. 161-166 (2009).

Alejandro Hernandez Arieta. Ryu Kato, Hiroshi Yokoi, Takashi Ohnishi, Tamio Arai: AnfMRI Study on the Effects of Electrical Stimulation as Biofeedback, Proceedings of the2006 IEEE/RSJ International Conference on Intelligent Robots and Systems (IROS2006), pp. 4336-4342 (2006).

* cited by examiner

FIG. 2

| RECORD No. | PREPROCESSING STIMULATION PARAMETERS | | |
|---|---|---|---|
| | BURST SIGNAL (Hz) | CARRIER SIGNAL (Hz) | DUTY RATIO (%) |
| 1 | 100 | 4k | 1 |
| 2 | 50 | 4k | 2 |
| 3 | 80 | 4k | 3 |
| 4 | 30 | 4k | 4 |
| ... | ... | ... | ... |

111a

FIG. 3
(a)
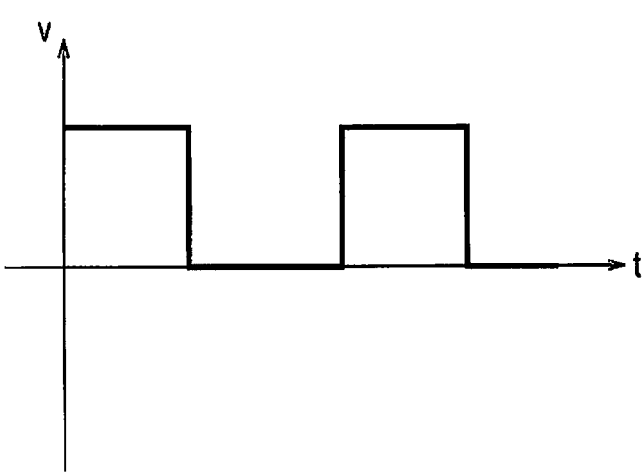
(b)
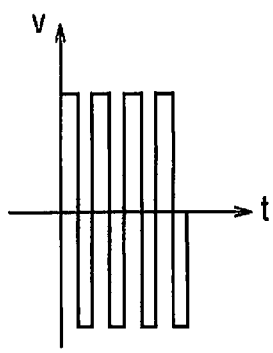
(c)
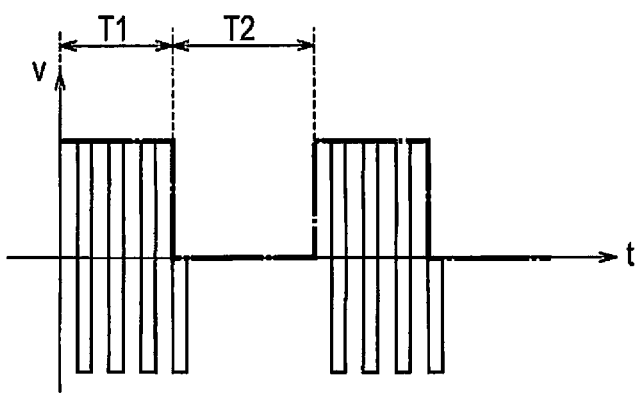

FIG. 9

| RECORD No. | STIMULATION PARAMETERS | | | EVALUATION RESULTS | | |
|---|---|---|---|---|---|---|
| | BURST SIGNAL (Hz) | CARRIER SIGNAL (Hz) | DUTY RATIO (%) | ATTACHED LOCATION | ACTIVATED LOCATION | t-VALUE |
| 1 | 100 | 4k | 1 | | | |
| 2 | 50 | 4k | 2 | | | |
| 3 | 80 | 4k | 3 | | | |
| 4 | 30 | 4k | 4 | | | |
| ... | ... | ... | ... | ... | ... | ... |

112a

| RECORD No. | PREPROCESSING STIMULATION PARAMETERS ||||| |
|---|---|---|---|---|---|
| | FIRST BURST SIGNAL(Hz) | SECOND BURST SIGNAL(Hz) | CARRIER SIGNAL (Hz) | STIMULATION SIGNAL RATIO | DUTY RATIO (%) |
| 1 | 100 | 50 | 4k | 7:3 | 1 |
| 2 | 100 | 50 | 4k | 8:2 | 1 |
| 3 | 100 | 50 | 4k | 9:1 | 1 |
| 4 | 100 | 50 | 4k | 5:5 | 1 |
| ... | ... | ... | ... | ... | ... |

| RECORD No. | PREPROCESSING STIMULATION PARAMETERS ||||| 
|---|---|---|---|---|---|
| | FIRST BURST SIGNAL(Hz) | SECOND BURST SIGNAL(Hz) | CARRIER SIGNAL(Hz) | STIMULATION SIGNAL RATIO | DUTY RATIO (%) |
| 1 | 100 | 50 | 4k | 7:3 | 1 |
| 2 | 100 | 50 | 4k | 8:2 | 1 |
| 3 | 100 | 50 | 4k | 9:1 | 1 |
| 4 | 100 | 50 | 4k | 5:5 | 1 |
| ... | ... | ... | ... | ... | ... |

(b) 112d

| RECORD No. | STIMULATION PARAMETERS ||||| EVALUATION RESULTS ||||
|---|---|---|---|---|---|---|---|---|---|
| | FIRST BURST SIGNAL(Hz) | SECOND BURST SIGNAL(Hz) | CARRIER SIGNAL(Hz) | STIMULATION SIGNAL RATIO | DUTY RATIO (%) | ATTACHED LOCATION | LOCATION t-VALUE | ANGLE DATA | MUSCLE ACTIVITY DATA |
| 1 | 100 | 50 | 4k | 7:3 | 1 | | | | |
| 2 | 100 | 50 | 4k | 8:2 | 1 | | | | |
| 3 | 100 | 50 | 4k | 9:1 | 1 | | | | |
| 4 | 100 | 50 | 4k | 5:5 | 1 | | | | |
| ... | ... | ... | ... | ... | ... | ... | ... | ... | ... |

STIMULATION SIGNAL GENERATION DEVICE AND STIMULATION SIGNAL GENERATION METHOD

TECHNICAL FIELD

The present invention relates to a stimulation signal generation device and a stimulation signal generation method for generating a stimulation signal to be used to assist walking exercise or finger exercise.

BACKGROUND ART

Cranial nerve paralysis or paralysis caused by sensorimotor system diseases takes a fundamental means of human life and significantly reduces convenience of daily life. Such physically handicapped persons are increasing year by year. Recently, studies have been made on various technologies for assisting the physically handicapped persons in their physical exercise such as walking.

The assistance of the physical exercise includes an assistance of actual exercise, and an assistance used in training for facilitating exercise (refer to Patent Literature 1, for example). Examples include (1) a method using an external mechanical force, (2) a method using invasive electrical stimulation, and (3) a noninvasive electrical stimulation method, and the method using the external mechanical force is currently in the mainstream.

Although the method using the electrical stimulation is also useful, the method is not much used because of problems such as: (i) the stimulation cannot exert its effect for a long time because a user gets used to the stimulation, (ii) the stimulation may cause pain, (iii) the stimulation cannot exert its effect for a long time due to muscle fatigue because of reverse recruitment which is caused by the stimulation directly applied to the muscle from the outside, and (iv) the stimulation is prone to cause convulsions.

CITATION LIST

Patent Literature

Patent Literature 1: Japanese Patent Application Publication No. 2008-67917

Non Patent Literature

Non Patent Literature 1: Alejandro Hernandez Arieta, Ryu Kato, Hiroshi Yokoi, Takashi Ohnishi, Tamio Arai: An fMRI Study on the Effects of Electrical Stimulation as Biofeedback, Proceedings of the 2006 IEEE/RSJ International Conference on Intelligent Robots and Systems (IROS2006), pp 4336-4342, 2006

SUMMARY OF INVENTION

Technical Problem

In view of the foregoing problems, the present invention provides a stimulation signal generation device and a stimulation signal generation method for generating a stimulation signal which sustains an exercise assist effect for long periods and causes no pain and convulsions.

Solution to Problem

A stimulation signal generation device according to a feature of the present invention includes a brain activity data acquisition unit configured to acquire data on activity of a human body's brain; a generator unit configured to generate a stimulation signal to be applied to a nerve corresponding to the specific brain region which is activated in order to move a joint of the human body, based on predetermined stimulation parameters or stimulation parameters determined from the data acquired by the brain activity data acquisition unit; and an output unit configured to output the stimulation signal generated by the generator unit.

According to the present invention, a stimulation signal which sustains an exercise assist effect for long periods and causes no pain and convulsions can be generated.

BRIEF DESCRIPTION OF DRAWINGS

FIG. 2 is a table of assistance in explaining an example of preprocessing data for use in the stimulation signal generation device of FIG. 1.

FIG. 3 is a chart of assistance in explaining signal superimposition in the stimulation signal generation device of FIG. 1.

FIG. 9 is a table of assistance in explaining an example of activity data for use in the stimulation signal generation device of FIG. 8.

FIG. 19 is tables illustrating examples of preprocessing data and activity data, respectively, for use in the stimulation signal generation device of FIG. 18.

DESCRIPTION OF EMBODIMENTS

Figure 1:
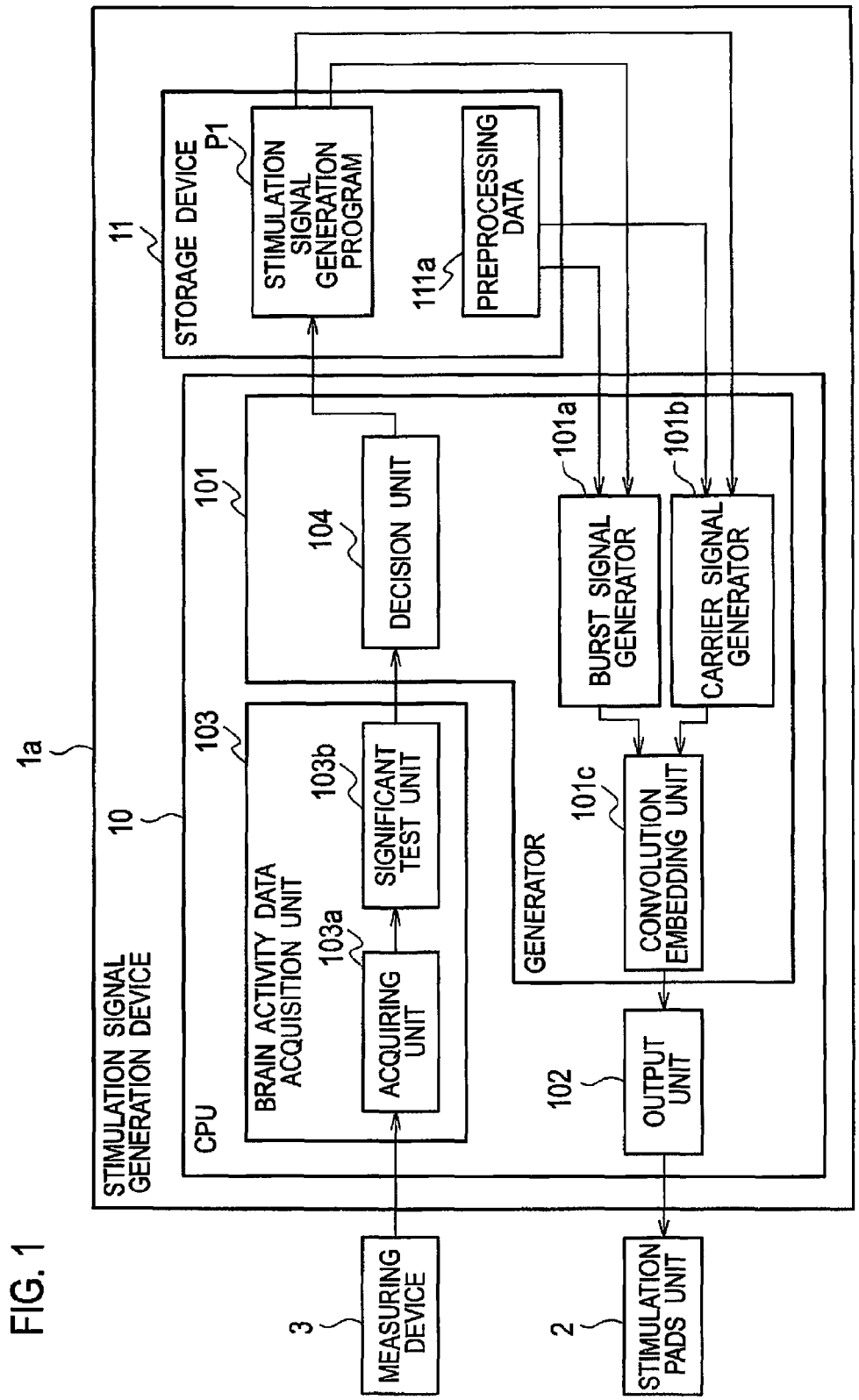
FIG. 1 is a block diagram of assistance in explaining a configuration of a stimulation signal generation device according to a first embodiment.

Description will be given below with reference to the drawings with regard to stimulation signal generation devices and stimulation signal generation methods according to embodiments of the present invention. The stimulation signal generation devices according to the embodiments of the present invention are each a device for generating a stimulation signal to be used to assist user's exercise. The stimulation signal generated by the stimulation signal generation device is applied to the user, for example when the user has difficulty in necessary movements for daily life due to having an upper motor neuron disorder caused by damage to a central nervous system, such as cranial nerve paralysis or paralysis caused by a sensorimotor system disease. The user is assisted in his or her exercise by being stimulated by a stimulus being transmitted along a nerve to the brain and from the brain to a muscle by the signal generated by the stimulation signal generation device. In the following description, the same configurations or the same processing is designated by the same reference numerals, and description of the same configurations or processing will be omitted.

[First Embodiment]

As illustrated in FIG. 1, a stimulation signal generation device 1a according to a first embodiment of the present invention includes a generator 101 configured to generate parameters of a stimulation signal to be applied, for the purpose of activating a specific brain region, to nerves (e.g. an afferent neuron and an efferent neuron) corresponding to the specific brain region (e.g. a somatosensory area, or a parietal association area or a prefrontal area around the somatosensory area) which is activated for the purpose of moving a joint of the human body, and configured to generate the stimulation signal according to the parameters, an output unit 102 configured to output the stimulation signal generated by the generator 101, and a brain activity data acquisition unit 103 configured to acquire data on activity of a brain when the stimulation signal is applied to the nerves of the human body.

The stimulation signal generation device 1a is configured so that the generator 101, the output unit 102 and the brain activity data acquisition unit 103 are implemented in a central processing unit (CPU) 10 as illustrated in FIG. 1, by installing a stimulation signal generation program P1 in an information processing apparatus including the CPU 10 and a storage device 11. The storage device 11 stores the stimulation signal generation program P1, and, in addition, preprocessing data 111a for use in determination of optimum stimulation parameters.

The state of damage to a nervous system or the state of paralysis varies from user to user. Also, the amount of subcutaneous fat varies from user to user, and also, stimulation (or frequency) to which users are sensitive varies according to skinfold thickness. Thus, the stimulation signal generation device 1a needs to apply a stimulation signal according to the user, when assisting the user's exercise. Therefore, the stimulation signal generation device 1a performs preprocessing to measure the state of user's brain activity with a stimulation signal applied under various conditions and select optimum conditions from obtained, measured results. The optimum conditions refer to conditions under which the brain activity becomes active without being suppressed. Also, the stimulation signal generation device 1a uses the optimum conditions to generate a stimulation signal and thereby assist the user's exercise.

The stimulation signal generation device 1a has connections to stimulation pads unit 2 configured to apply the stimulation signal generated by the stimulation signal generation device 1a to the user when performing the preprocessing or assisting the user's exercise, and a measuring device 3 configured to measure the state of user's brain activity, which are collectively used as an exercise assist system.

The stimulation pads unit 2 is a device attached to the skin of the human body to be assisted in its exercise by the stimulation signal generation device 1a, and configured to apply the stimulation signal through the skin. The stimulation pads unit 2 is placed in the vicinity of a joint determined according to the state of the user and movement to be assisted, and applies stimulation to nerves in the vicinity of the joint. For example, the stimulation pads unit 2 is attached in the vicinity of a waist, knee or ankle joint or the like when assisting walking movement, or is attached in the vicinity of a shoulder, elbow or wrist joint or the like when assisting hand movement. The stimulation pads unit 2 is formed for example of an electroconductive gel and an electrode connected to the electroconductive gel, and can expand an input signal of a surface distribution type coming in from the stimulation signal generation device 1a and apply the signal to the user's nerves through the skin thereby to stimulate the user's nerves. However, the stimulation pads unit 2 is not limited to being formed of the electroconductive gel and the electrode connected thereto but may use electromagnetic induction or vibration to apply the input signal from the stimulation signal generation device 1a to the user's nerves and thereby stimulate the user's nerves.

Specifically, the stimulation pads unit 2 is attached at a location where stimulation is applied to both the afferent neuron and the efferent neuron. Thus, the stimulation pads unit 2 is attached at the location where the stimulation is applied to both the afferent neuron and the efferent neuron, and thereby, the stimulation generated by the stimulation signal generation device 1a and applied to the user is transmitted through the nerves to the brain. When assisting finger exercise for example, the stimulation pads unit 2 is attached to the user's extensor pollicis longus muscle, extensor indicis muscle, extensor carpi radialis longus muscle, extensor carpi ulnaris muscle or extensor digitorum communis muscle or the like. Also, when assisting walking for example, the stimulation pads unit 2 is attached to the user's quadriceps femoris muscle, tibialis anterior muscle, extensor digitorum longus muscle, peroneal muscle, extensor hallucis longus muscle, biceps femoris muscle, semimembranous muscle, semitendinous muscle or soleus muscle or the like.

Here, the stimulation signal applied by the stimulation pads unit 2 is not transmitted directly to the muscle but is transmitted from the skin to the nerve, from the nerve to the brain, and then from the brain to the muscle thereby to exercise the muscle. In other words, instead of making the muscle exercise through reverse recruitment by applying stimulation directly to the muscle thereby as is the case with an exercise assist device which has heretofore been used, the stimulation signal generation device 1a can make the muscle exercise through forward recruitment involving transmission from the nerve to the brain and then from the brain to the muscle. In this regard, when a high voltage (on the order of 50 to 200 V, for example) is used to apply stimulation, the stimulation can be applied directly to the muscle, while on the other hand, when a relatively low voltage (for example, a voltage on the order of 9 to 100 V, which does not tend to cause the user to feel pain) is used to apply stimulation, the stimulation can be applied to the nerve through the skin and the muscle. In the case of the upper motor neuron disorder caused by the damage to the central nervous system, a peripheral nervous system and the muscle function, and therefore, the stimulation signal generation device 1a can exercise the muscle by applying the stimulation signal as an alternative to a command from the spinal cord or the brain.

The measuring device 3 is a device for measuring the brain activity, and an MRI (magnetic resonance imaging) apparatus, an electroencephalograph or a near-infrared brain measurement devices or the like, for example, is available for use as the measuring device 3; however, the measuring device 3 is described here as being the MRI apparatus. The MRI apparatus can obtain image data for determination of the brain activity with the user fixed to a cot. When the MRI apparatus is used as the measuring device 3, therefore, description will be given assuming that the brain activity is measured only during the preprocessing and the stimulation signal generation device 1a and the measuring device 3 are connected together only during the preprocessing.

The preprocessing data 111a stored in the storage device 11 is a list of preprocessing stimulation parameters as the conditions of the stimulation signal to be applied to the user in the preprocessing for selecting the optimum conditions of the stimulation signal for the user. For example, the preprocessing stimulation parameters include the value of the frequency of a burst signal, the value of the frequency of a carrier signal, and the duty ratio for the output timing of the stimulation signal, as illustrated in FIG. 2.

Upon receipt of input of an operation signal to request the start of the preprocessing or movement assist processing through an input device (unillustrated) such as an operation button, the generator 101 generates the stimulation signal by using values according to the operation. For example, in the preprocessing, the generator 101 reads a target value from the preprocessing data 111a stored in the storage device 11 and uses the value. Also, in the movement assist processing, the generator 101 uses a value specified by the stimulation signal generation program P1 stored in the storage device 11. For example, the generator 101 includes a burst signal generator 101a, a carrier signal generator 101b and a convolution embedding unit 101c in order to execute the above processing. Further, the generator 101 includes a decision unit 104 configured to determine optimum values (or parameters) for stimulation signal generation.

In the preprocessing, the burst signal generator 101a reads the preprocessing data 111a from the storage device 11, extracts the values of the preprocessing stimulation parameters, and generates the burst signal. Also, in the movement assist processing, the burst signal generator 101a generates the burst signal by using the values of the parameters specified by the stimulation signal generation program P1.

The burst signal generated by the burst signal generator 101a is a signal as illustrated for example in Part (a) of FIG. 3, the parameters of which is a frequency (of 15 to 200 Hz, for example). The burst signal is the signal for activating a brain region for use in a specific exercise (or movement) to be assisted by the stimulation signal generation device 1a. Specifically, the brain region for use in the exercise is the somatosensory area, or part of the parietal association area or the prefrontal area around the somatosensory area.

In the preprocessing, the carrier signal generator 101b reads the preprocessing data 111a from the storage device 11, extracts the values of the preprocessing stimulation parameters, and generates the carrier signal. Also, in the movement assist processing, the carrier signal generator 101b generates the carrier signal by using the values of the parameters specified by the stimulation signal generation program P1. The carrier signal is what is called a carrier signal, and is a signal formed of a carrier alone without data. Specifically, the carrier signal is formed of a rectangular wave having a higher frequency (of a few kilohertz to 20 kilohertz, for example) than the frequency of the burst signal, as illustrated by way of example in Part (b) of FIG. 3.

The convolution embedding unit 101c superimposes the carrier signal generated by the carrier signal generator 101b on the burst signal generated by the burst signal generator 101a, thereby to generate a stimulation signal as illustrated in Part (c) of FIG. 3. Also, the convolution embedding unit 101c outputs stimulation data by outputting the generated stimulation, signal in conjunction with the duty ratio (T2/(T1+T2)) included in the corresponding preprocessing stimulation parameters or stimulation parameters.

Incidentally, the stimulation signal generation device 1a is described here as using the burst signal and the carrier signal to output the stimulation signal obtained by superimposing the carrier signal on the burst signal; however, even when the burst signal is used as the stimulation signal without the use of the carrier signal, stimulation required to assist exercise can be applied to the user.

When the carrier signal having a higher frequency than that of the burst signal is superimposed on the burst signal by the convolution embedding unit 101c, the amount of voltage drop on the skin surface is reduced and hence pain can be reduced, as compared to when the burst signal applies stimulation directly to the user. Also, the amount of voltage drop on the user's muscle increases as the amount of voltage drop on the skin surface decreases. As a result, the amount of inrush current to the nerve which contracts the muscle is increased, so that electrical stimulation sufficient to assist exercise can be applied.

The output unit 102 outputs the stimulation signal contained in the stimulation data outputted by the generator 101, to the stimulation pads unit 2, according to the duty ratio contained in the stimulation data. The stimulation pads unit 2 outputs the stimulation signal coming in from the output unit 102 thereby to apply stimulation to the user. In this process, the output unit 102 outputs the stimulation signal at a predetermined time for each preprocessing or exercise assist processing. When the signal outputted by the output unit 102 applies stimulation to both the afferent neuron and the efferent neuron, the stimulation can be transmitted to the somatosensory area of the brain or part of the parietal association area or the prefrontal area around the somatosensory area thereby to exercise the muscle.

Figure 4:
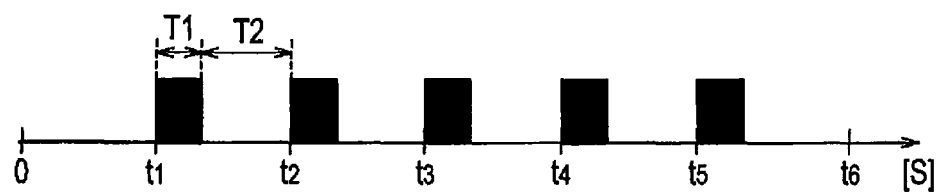
FIG. 4 is a chart of assistance in explaining the outputting of the signal in the stimulation signal generation device of FIG. 1.

FIG. 4 illustrates an example in which the output unit 102 applies stimulation to the user five times at predetermined intervals (for example, at intervals of five seconds). In this case, time T1 at which the stimulation is outputted and time 12 at which the outputting of the stimulation is stopped are predetermined. The measuring device 3 captures an image in accordance with the outputting of the stimulation signal. The stimulation signal generation device 1a repeats the same processing plural times since it is desirable that larger amounts of image data be used to generate activity data 112a. For example, the stimulation signal generation device 1a can obtain image data in amounts corresponding to forty images by repeating a session of capture of five images eight times.

Also, in the case of the exercise assist processing, it is necessary to apply stimulation to the user so that the exercise can be continuously assisted. Therefore, the output unit 102 outputs the stimulation signal at a predetermined time, such as at regular intervals (for example, at intervals of five seconds), between the input of the operation signal to start the assist processing and the input of an operation signal to end the assist processing so that the stimulation can be continuously applied.

When, during the preprocessing, the output unit 102 outputs the stimulation signal and thereby the stimulation pads unit 2 applies stimulation to the user, the brain activity data acquisition unit 103 acquires data on the brain activity of the user to which the stimulation is applied. For example, the brain activity data acquisition unit 103 includes an acquiring unit 103a and a significant test unit 103b.

The acquiring unit 103a acquires plural image data captured by the measuring device 3 in accordance with the time at which the stimulation signal is outputted by the output unit 102. The plural image data is images captured continuously at predetermined intervals. The image acquired from the measuring device 3 is an image as illustrated by way of example in FIG. 5. In the example of the image (e.g. an MRI image) illustrated in FIG. 5, the amount of deoxyhemoglobin can be used to determine an activated location in the brain by color tone, and a marked area X is a location identified as being activated.

The significant test unit 103b uses a significant test (for example, a t-test) to determine a t-value and a most highly activated location in the user's brain, as the data on the brain activity, from the plural acquired image data. The sensory area (e.g. the somatosensory area) of the brain corresponds at the vertex in turn to the legs, the trunk, the hands and the face. For example, for leg movement assist, it is most desirable that a location identified as being activated by the color tone in the images acquired by the acquiring unit 103a under application of simulation to the user be only a location corresponding to the legs, and the t-value determined from the plural images is maximized. If a location corresponding to the trunk, in addition to the location corresponding to the legs, is also determined by the color tone in the images, the trunk is also judged as being given the stimulation, which is undesirable, and also, the t-value is small.

Figure 5:
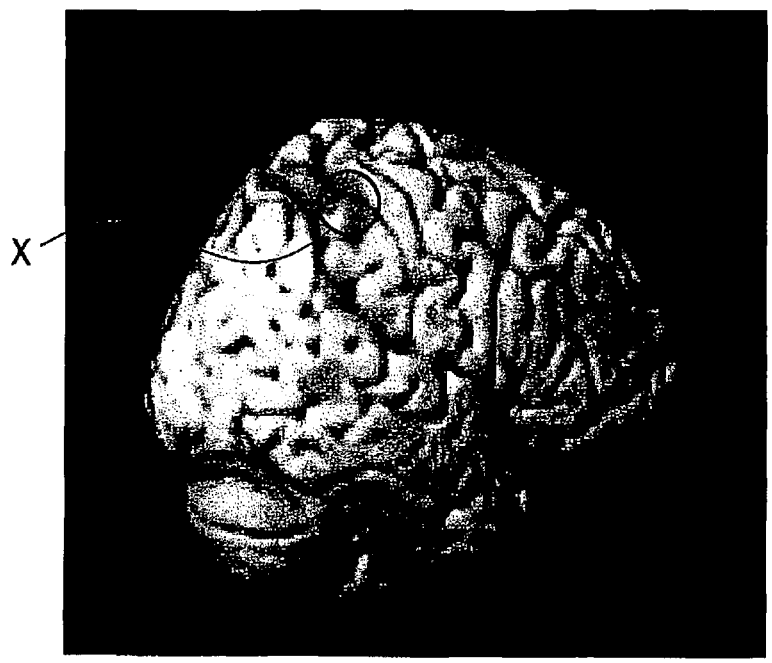
FIG. 5 is a representation of assistance in explaining an example of image data for use in the stimulation signal generation device of FIG. 1.

Incidentally, description is here given taking an example in which the t-test is used as the significant test to determine the t-value as a significant test value; however, a significant test unit which uses a z-test as the significant test to determine a z-value as the significant test value may be used. Also, the example illustrated in FIG. 5 is two-dimensional brain data; however, actually, the image data acquired from the measuring device 3 may be used to determine a three-dimensional location in the brain.

The decision unit 104 compares plural values (for example, t-values) obtained by the significant test unit 103b, extracts an optimum value, and determines that conditions (or parameters) under which the optimum value is obtained are conditions for use in the movement assist processing. Also, the decision unit 104 writes the determined conditions to the stimulation signal generation program P1 stored in the storage device 11.

As described above, conditions selected from among plural conditions by the decision unit 104 are used as the parameters for use in the movement assist processing, and thereby, the stimulation signal generation device 1a can generate the stimulation signal according to the user to assist the user's exercise.

[Preprocessing]

Figure 6:
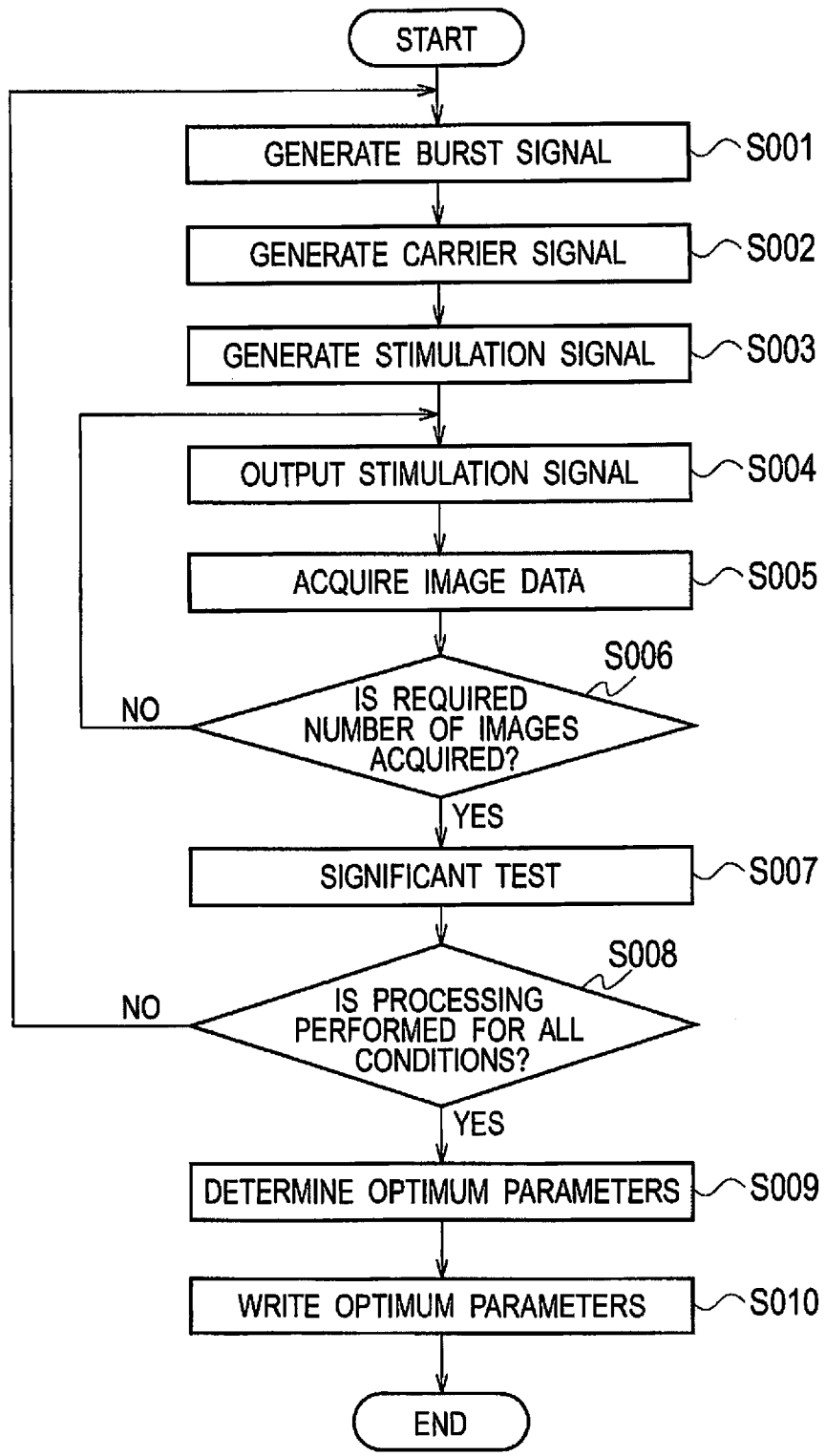
FIG. 6 is a flowchart of assistance in explaining preprocessing in the stimulation signal generation device of FIG. 1.

Firstly, description will be given with reference to a flowchart illustrated in FIG. 6 with regard to the preprocessing which the stimulation signal generation device 1a according to the first embodiment performs before assisting exercise. When assisting the user's exercise, the stimulation signal generation device 1a performs the preprocessing to predetermine conditions (or parameters) for the stimulation signal for the user in order to apply optimum stimulation to the user as an assist object. In the preprocessing, the user is in a state in which the stimulation pads unit 2 is attached to the skin to apply stimulation to the user, and is in a state in which brain image data can be captured by the measuring device 3 when the stimulation is applied to the user.

Upon receipt of input of the operation signal to start the preprocessing, the burst signal generator 101a of the stimulation signal generation device 1a extracts the value of the burst signal from the preprocessing data 111a, and generates the burst signal according to the extracted value (at step S001). Also, the carrier signal generator 101b extracts the value of the carrier signal from the preprocessing data 111a, and generates the carrier signal according to the extracted value (at step S002). The convolution embedding unit 101c generates a stimulation signal by superimposing the carrier signal generated at step S002 on the burst signal generated at step S001, and outputs stimulation data by outputting the stimulation signal in conjunction with the duty ratio (at step S003).

After that, the output unit 102 outputs the stimulation signal generated at step S003 to the stimulation pads unit 2 according to the duty ratio contained in the stimulation data (at step S004). Thereby, the stimulation pads unit 2 applies stimulation to the user's nerve according to the stimulation signal.

When the output unit 102 outputs the stimulation signal and thereby the stimulation pads unit 2 applies the stimulation to the user, the brain activity data acquisition unit 103 acquires image data captured by the measuring device 3 (at step S005). When the image data is acquired in amounts corresponding to the required number of images for the significant test (YES at step S006), the significant test unit 103b obtains a test result by the significant test (at step S007). Meanwhile, when the image data is not acquired in amounts corresponding to the required number of images (NO at step S006), the stimulation signal generation device 1a repeats the processing of steps S004 and S005.

The obtained test result is temporarily stored in the storage device 11 or memory (unillustrated). When the processing of steps S001 to S007 is performed for all conditions specified by the preprocessing (YES at step S008), the decision unit 104 determines that conditions under which the t-value is maximized are optimum parameters, from all values obtained by the significant test unit 103b (at step S009). Also, the decision unit 104 writes the values determined as the optimum parameters, as the parameters for use in the movement assist processing, to the stimulation signal generation program P1 stored in the storage device 11 (at step S010).

Meanwhile, when there is a condition for which the processing is not completed (NO at step S008), the stimulation signal generation device 1a repeats the processing of steps S001 to S007 until test results are obtained for all conditions.

Also, the preprocessing data for use in the preprocessing is predetermined by using general stimulation parameters. In this case, the preprocessing stimulation parameters may vary according to sex or age.

[Assist Processing]

Figure 7:
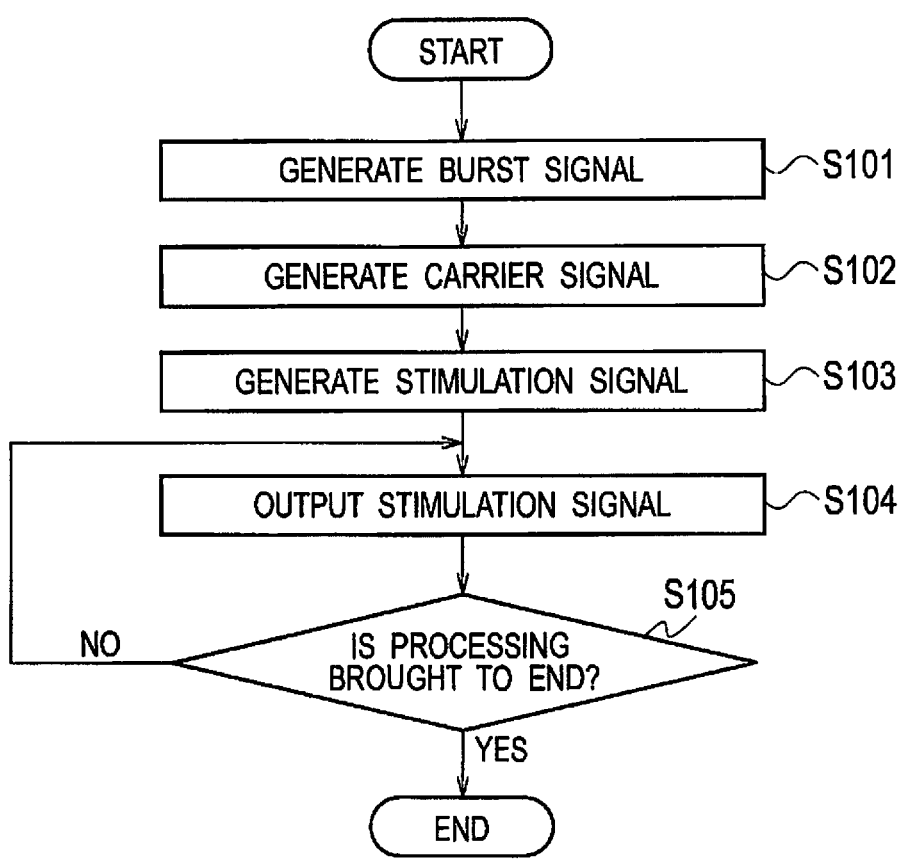
FIG. 7 is a flowchart of assistance in explaining assist processing in the stimulation signal generation device of FIG. 1.

Next, description will be given with reference to a flowchart illustrated in FIG. 7 with regard to the assist processing for assisting the user's exercise, which the stimulation signal generation device 1a according to the first embodiment performs after having performed the preprocessing to write the optimum conditions (or parameters) to the stimulation signal generation program P1.

In the stimulation signal generation device 1a, upon receipt of input of the operation signal to start the exercise assist, the burst signal generator 101a generates the burst signal according to the value of the burst signal specified by the stimulation signal generation program P1 (at step S101). Also, the carrier signal generator 101b generates the carrier signal according to the value of the carrier signal specified by the stimulation signal generation program P1 (at step S102).

Then, the convolution embedding unit 101c generates a stimulation signal by superimposing the carrier signal generated at step S102 on the burst signal generated at step S101, and outputs stimulation data by outputting the stimulation signal in conjunction with the duty ratio (at step S103).

After that, the output unit 102 outputs the stimulation signal generated at step S103 to the stimulation pads unit 2 according to the duty ratio contained in the stimulation data (at step S104). Thereby, the stimulation pads unit 2 applies stimulation to the user's nerve according to the stimulation signal. Also, the output unit 102 repeats the processing of step S104 until it receives input of the operation signal to end the assist processing (at step S105).

As described above, the stimulation signal generation device 1a assists the user's exercise by using the stimulation signal transmitted through the skin and the muscle to the nerve. Also, the stimulation signal generation device 1a generates the optimum stimulation signal according to the user. When the stimulation signal generation device 1a is used to assist the exercise, therefore, the user suffers no pain and convulsions, and an exercise assist effect can also be sustained for long periods.

Also, the stimulation signal generation device 1a applies stimulation for training for the user's somatosensory area or the association area or the prefrontal area around the somatosensory area, and thereby, the activity of the somatosensory area or the association area or the prefrontal area around the somatosensory area becomes active, which in turn makes it easy for the user to do exercise even when stimulation is not applied. Also, the stimulation signal generation device 1a applies stimulation thereby to enable restrengthening not only the affected side but also the unaffected side.

Incidentally, in the stimulation signal generation device 1a, it is most desirable that the preprocessing be performed for each user to determine optimum parameters for use; however, parameters obtained by performing the preprocessing on a certain user may be used for a different user (or a third party) to perform the assist processing. In this case, it is desirable that parameters obtained by performing the preprocessing on a user similar in conditions (e.g. a symptom, a body type, age, sex, etc.) be used for a different user to perform the assist processing.

[Modification]

Figure 8:
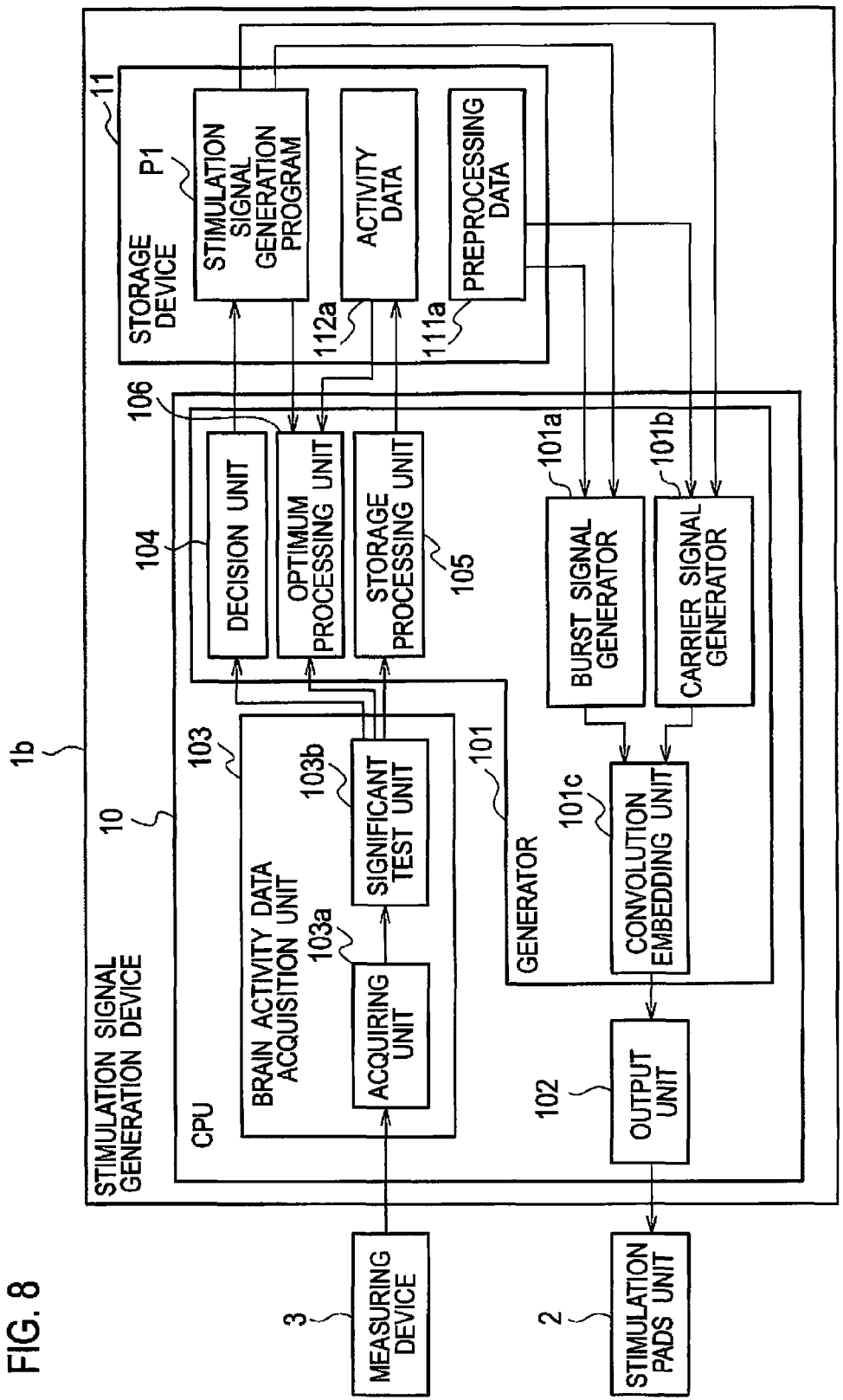
FIG. 8 is a block diagram of assistance in explaining a configuration of a stimulation signal generation device according to Modification.

As illustrated in FIG. 8, a stimulation signal generation device 1b according to Modification of the first embodiment is different in that the generator 101 includes a storage processing unit 105 and an optimization processing unit 106 and the storage device 11 stores the activity data 112a, as compared to the stimulation signal generation device 1a described above with reference to FIG. 1.

The activity data 112a is a list of histories of the state of activity under application of stimulation to the user. Specifically, as illustrated by way of example in FIG. 9, the activity data 112a includes stimulation parameters as conditions for the stimulation signal to be applied to the user, an attached location to determine a location on the user at which the stimulation pads unit 2 is attached, and evaluation results as values obtained by evaluating an activated location and activity in the brain of the user to which the stimulation signal determined by the stimulation parameters is applied, and the stimulation parameters, the attached location and the evaluation results are related to one another.

The storage processing unit 105 outputs the results of the significant test obtained by the brain activity data acquisition unit 103, in conjunction with conditions for outputting the stimulation signal, as the activity data 112a, which is then stored in the storage device 11. Specifically, the values of the "burst signal," the "carrier signal" and the "duty ratio" as the stimulation parameters as the conditions for outputting the stimulation signal, the "attached location" at which the stimulation pads unit 2 is attached, and the values of the "activated location" and the "t-value" as the evaluation results as the results of the significant test are related to one another to form the activity data 112a.

[Preprocessing]

Figure 10:
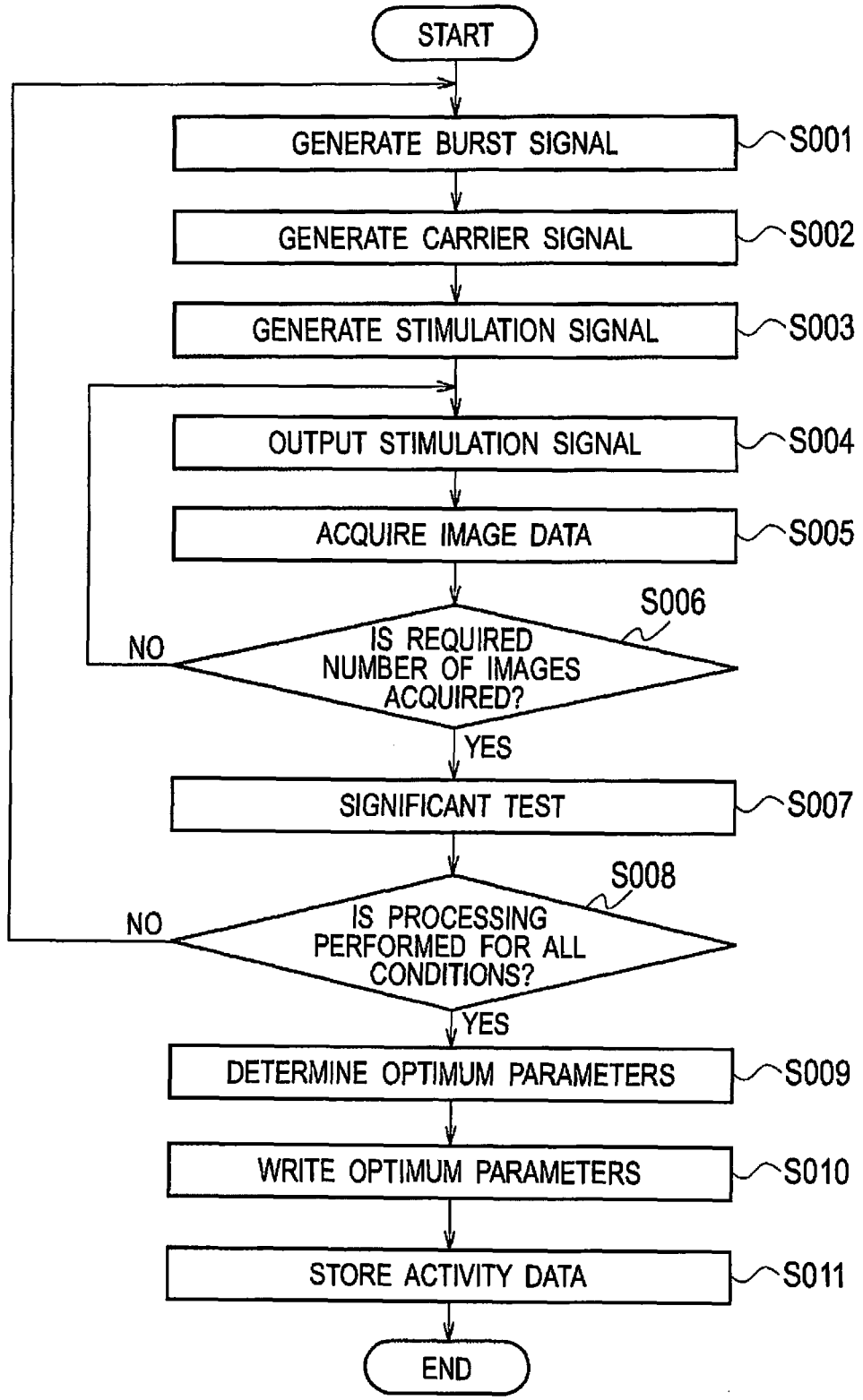
FIG. 10 is a flowchart of assistance in explaining the preprocessing in the stimulation signal generation device of FIG. 8.

Description will be given with reference to a flowchart illustrated in FIG. 10 with regard to the preprocessing which the stimulation signal generation device 1b according to Modification performs before assisting movement. As illustrated in FIG. 10, the processing of steps S001 to S010 is the same as the processing described above with reference to FIG. 6.

In the stimulation signal generation device 1b, when the optimum parameters are written to the stimulation signal generation program P1 at step S010, the storage processing unit 105 relates plural values obtained by the significant test at step S007 to parameters under which the values are obtained, thereby to form the activity data 112a, which is then stored in the storage device 11 (at step S011).

[Assist Processing]

Next, description will be given with reference to a flowchart illustrated in FIG. 11 with regard to processing for assisting movement while updating parameters for use in the stimulation signal generation program P1, which is performed by the stimulation signal generation device 1b according to Modification. The measuring device 3 connected to the stimulation signal generation device 1b according to Modification is described here as being a device capable of measuring the brain activity while the user is doing exercise, such as the electroencephalograph or the near-infrared brain measurement devices, rather than the MRI apparatus.

Figure 11:
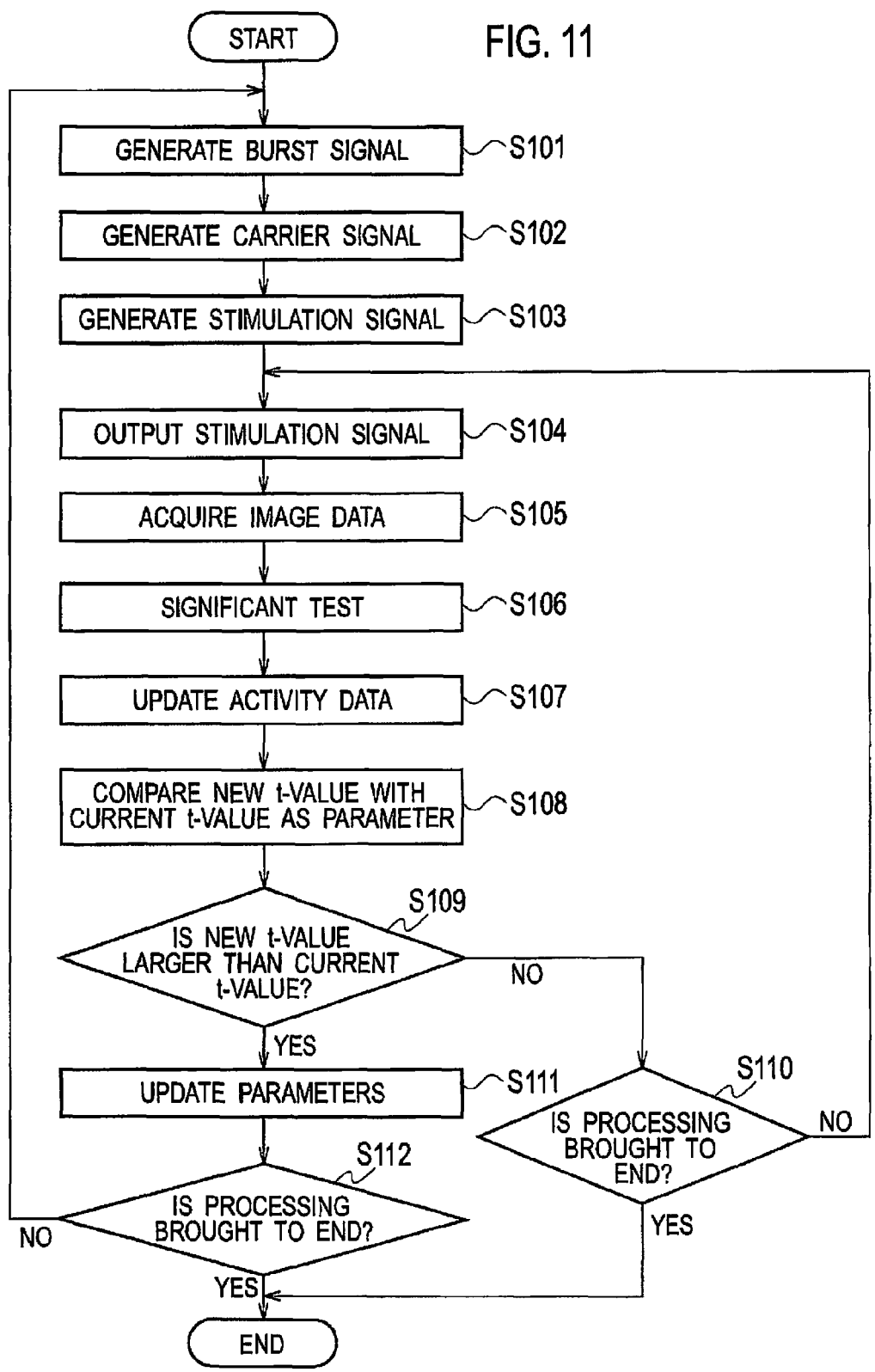
FIG. 11 is a flowchart of assistance in explaining the assist processing in the stimulation signal generation device of FIG. 8.

As illustrated in FIG. 11, the processing of steps S101 to S104 is the same as the processing described above with reference to FIG. 7. In the stimulation signal generation device 1b, when the stimulation signal is outputted at step S104, the acquiring unit 103a acquires image data from the measuring device 3 (at step S105). After that, the significant test unit 103b executes the significant test (at step S106).

The storage processing unit 105 updates the activity data 112a stored in the storage device 11, by adding a newly obtained result of the significant test, and parameters under which the value of the result is obtained (at step S107).

Also, the optimization processing unit 106 performs a comparison between the t-value as the parameter being used in the stimulation signal generation program P1 and the t-value obtained newly by the significant test (at step S108). When the result of the comparison performed at step S108 shows that the newly obtained t-value is smaller than the t-value as the parameters being currently used in the stimulation signal generation program P1 (NO at step S109), the processing returns to step S104 if the assist processing is not brought to an end (NO at step S110).

Meanwhile, when the result of the comparison performed at step S108 shows that the newly obtained t-value is larger than the t-value as the parameters being currently used in the stimulation signal generation program P1 (YES at step S109), the values in the stimulation signal generation program P1 are overwritten with the newly obtained t-value and the values of parameters under which the t-value is obtained (at step S111). After that, if the assist processing is not brought to an end, the processing returns to step S101 (at step S112).

Incidentally, here, at step S111, the storage processing unit 105 updates the parameters in the stimulation signal generation program P1 by overwriting the parameters with the newly obtained values, and the updated parameters are used for stimulation signal generation; however, when the brain activity can be measured at the same time that the stimulation signal is outputted, the burst signal and the carrier signal may be directly generated without overwriting the stimulation signal generation program P1.

As described above, the stimulation signal generation device 1b assists the user's exercise by using the stimulation signal transmitted through the skin and the muscle to the nerve. Also, the stimulation signal generation device 1b generates the optimum stimulation signal according to the user. When the stimulation signal generation device 1b is used to assist the exercise, therefore, the user suffers no pain and convulsions, and the exercise assist effect can also be sustained for long periods.

Also, the stimulation signal generation device 1b applies stimulation for training for the user's somatosensory area or the association area or the prefrontal area around the somatosensory area, and thereby, the activity of the somatosensory area or the association area or the prefrontal area around the somatosensory area becomes active, which in turn makes it easy for the user to do exercise even when stimulation is not applied. Also, the stimulation signal generation device 1b applies stimulation thereby to enable restrengthening not only the affected side but also the unaffected side.

Incidentally, also in the stimulation signal generation device 1b, it is most desirable that the preprocessing be performed for each user to determine optimum parameters for use; however, parameters obtained by performing the preprocessing on a certain user may be used for a different user (or a third party) to perform the assist processing. In this case, it is desirable that parameters obtained by performing the preprocessing on a user similar in conditions (e.g. a symptom, a body type, age, sex, etc.) be used for a different user to perform the assist processing.

[Second Embodiment]

Figure 12:
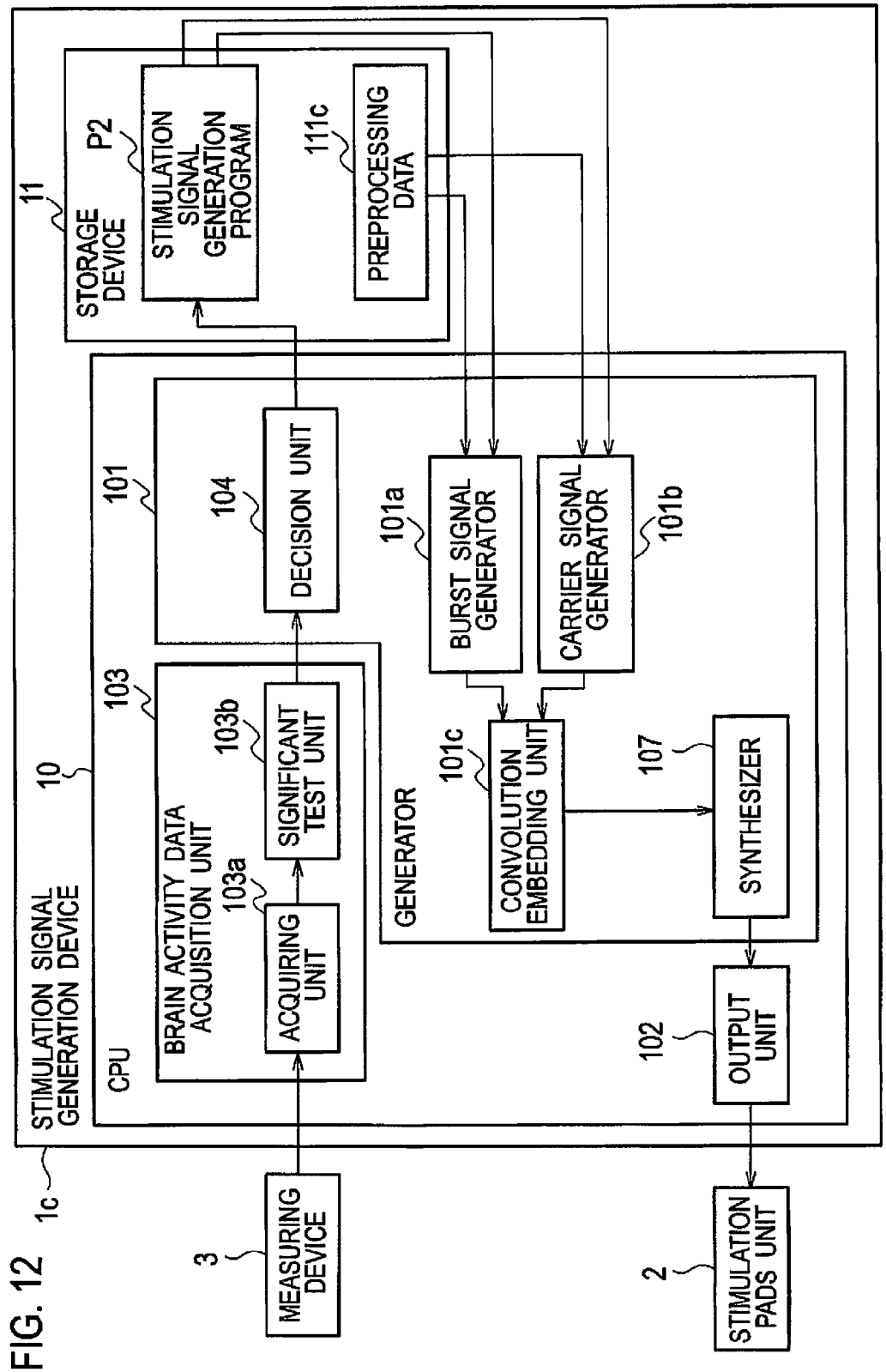
FIG. 12 is a block diagram of assistance in explaining a configuration of a stimulation signal generation device according to a second embodiment.

As illustrated in FIG. 12, a stimulation signal generation device 1c according to a second embodiment of the present invention is different in including a synthesizer 107, as compared to the stimulation signal generation device 1a described above with reference to FIG. 1. The stimulation signal generation device 1c is configured so that the generator 101, the output unit 102, the brain activity data acquisition unit 103, the decision unit 104 and the synthesizer 107 are implemented in the central processing unit (CPU) 10 as illustrated in FIG. 12, by installing a stimulation signal generation program P2 in the information processing apparatus including the CPU 10 and the storage device 11.

The stimulation signal generation device 1c generates stimulations of plural different frequencies, and applies the stimulations of the different frequencies in sequence. The application of the stimulations of the different frequencies makes it difficult for the user to get used to the stimulation and hence enhances a sustaining effect, as compared to the application of stimulation of a single frequency for a long time.

In order to apply the stimulations of the plural frequencies to the user, the stimulation signal generation device 1c uses preprocessing data 111c as the preprocessing stimulation parameters. As illustrated for example in FIG. 13, the preprocessing stimulation parameters include the value of the frequency of a first burst signal, the value of the frequency of a second burst signal, the value of the frequency of the carrier signal, a stimulation signal ratio as a ratio at which a first stimulation signal and a second stimulation signal are synthesized, and the duty ratio for the output timing of the stimulation signal, and the preprocessing stimulation parameters are related to one another.

Incidentally, here, the measuring device 3 connected to the stimulation signal generation device 1c may be the device capable of measuring the brain activity while the user is doing exercise, such as the electroencephalograph or the near-infrared brain measurement devices, besides the MRI apparatus.

The burst signal generator 101a reads plural burst signal frequency values from the preprocessing data 111c or the stimulation signal generation program P2, and generates the burst signals of plural frequencies. Also, the convolution embedding unit 101c generates stimulation signals by superimposing the carrier signal on the burst signals generated by the burst signal generator 101a. Therefore, when the burst signal generator 101a generates the first burst signal and the second burst signal having different frequencies, the convolution embedding unit 101c generates the first stimulation signal obtained by superimposing the carrier signal on the first burst signal, and the second stimulation signal obtained by superimposing the carrier signal on the second burst signal.

The synthesizer 107 synthesizes the plural stimulation signals generated by the generator 101. In this process, the synthesizer 107 synthesizes the first stimulation signal and the second stimulation signal at a ratio specified by the preprocessing data 111c or the stimulation signal generation program P2. For example, when the stimulation signal ratio stands at 7 to 3, a synthetic signal is generated in which the ratio of the first stimulation signal to the second stimulation signal is seven to three. The output unit 102 extracts the value of the duty ratio from the preprocessing data 111c, and provides an output to the stimulation pads unit 2 according to the extracted value.

Incidentally, after the synthesizer 107 has synthesized the first burst signal and the second burst signal, the convolution embedding unit 101c may superimpose the carrier signal on the synthesized burst signal. Alternatively, the stimulation signal generation device 1c may also use the first burst signal as the first stimulation signal and use the second burst signal as the second stimulation signal without the use of the carrier signal.

Figures 13, 14:
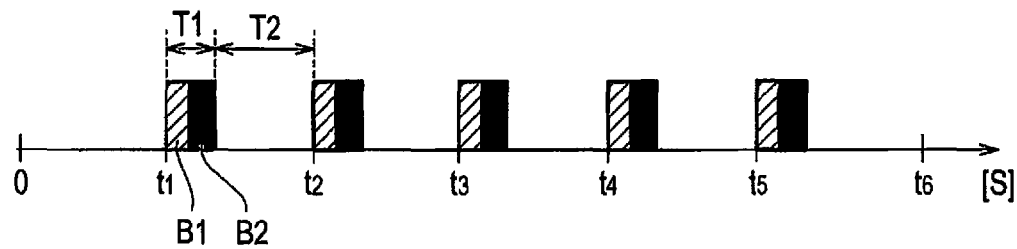
FIG. 13 is a table illustrating an example of preprocessing data for use in the stimulation signal generation device of FIG. 12.
FIG. 14 is a chart of assistance in explaining the outputting of the signal in the stimulation signal generation device of FIG. 12.

The output unit 102 receives input of stimulation data including a stimulation signal obtained by synthesizing a first stimulation signal B1 and a second stimulation signal B2, and the duty ratio, as illustrated by way of example in FIG. 14, and outputs the stimulation signal according to the duty ratio. As in the case of FIG. 4, FIG. 14 also illustrates an example of a session in which five images are captured while stimulation is applied to the user five times at a predetermined time, and image data in amounts corresponding to forty images can be obtained by repeating the session eight times.

Figure 15:
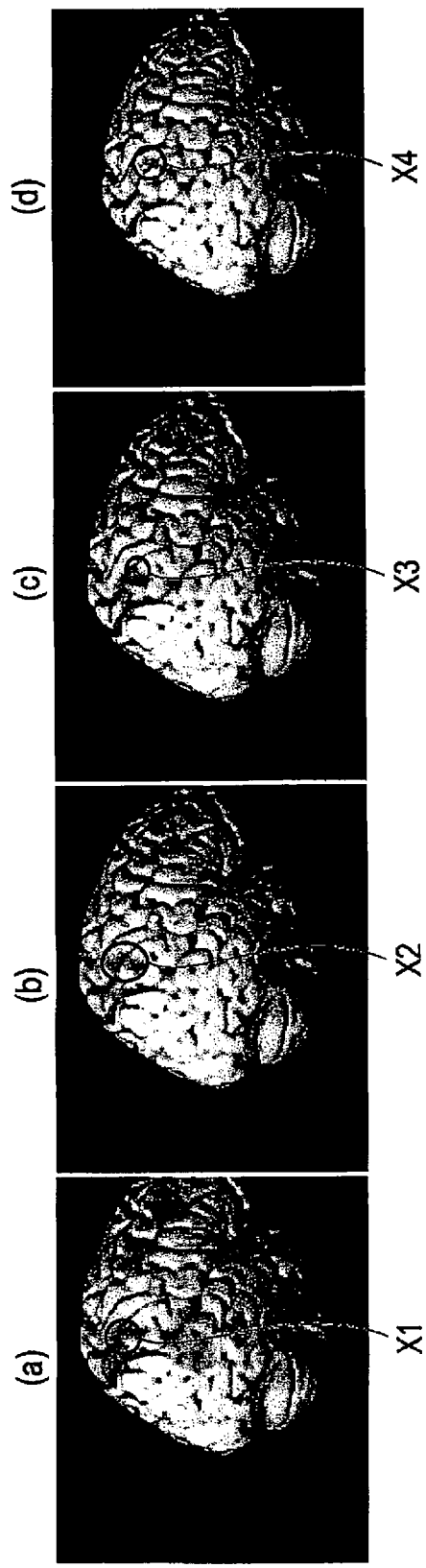
FIG. 15 is a representation of assistance in explaining an example of image data for use in the stimulation signal generation device of FIG. 12.

The stimulation signal generation device 1c performs the preprocessing in which image data is obtained under plural conditions, such as different combinations of stimulation frequencies and different ratios, thereby to determine optimum conditions. For instance, FIG. 15 illustrates, by way of example, images obtained when the first stimulation signal B1 has a frequency of 100 Hz and the second stimulation signal B2 has a frequency of 50 Hz. FIG. 15 illustrates, by way of example, the images obtained when the ratio of the first stimulation signal B1 to the second stimulation signal B2 is five to five (refer to Part (a) of FIG. 15), when the ratio is seven to three (refer to Part (b) of FIG. 15), when the ratio is eight to two (refer to Part (c) of FIG. 15), and when the ratio is nine to one (refer to Part (d) of FIG. 15), respectively.

When the significant test unit 103b determines the t-values of activated locations X1 to X4 obtained from the image data of FIG. 15 and compares the t-values, the highest value is obtained when the ratio of B1 to B2 is seven to three as illustrated in Part (b) of FIG. 15. Therefore, a decision is made that, of four conditions, a condition where the ratio of B1 to B2 is seven to three is an optimum condition.

[Preprocessing]

Figure 16:
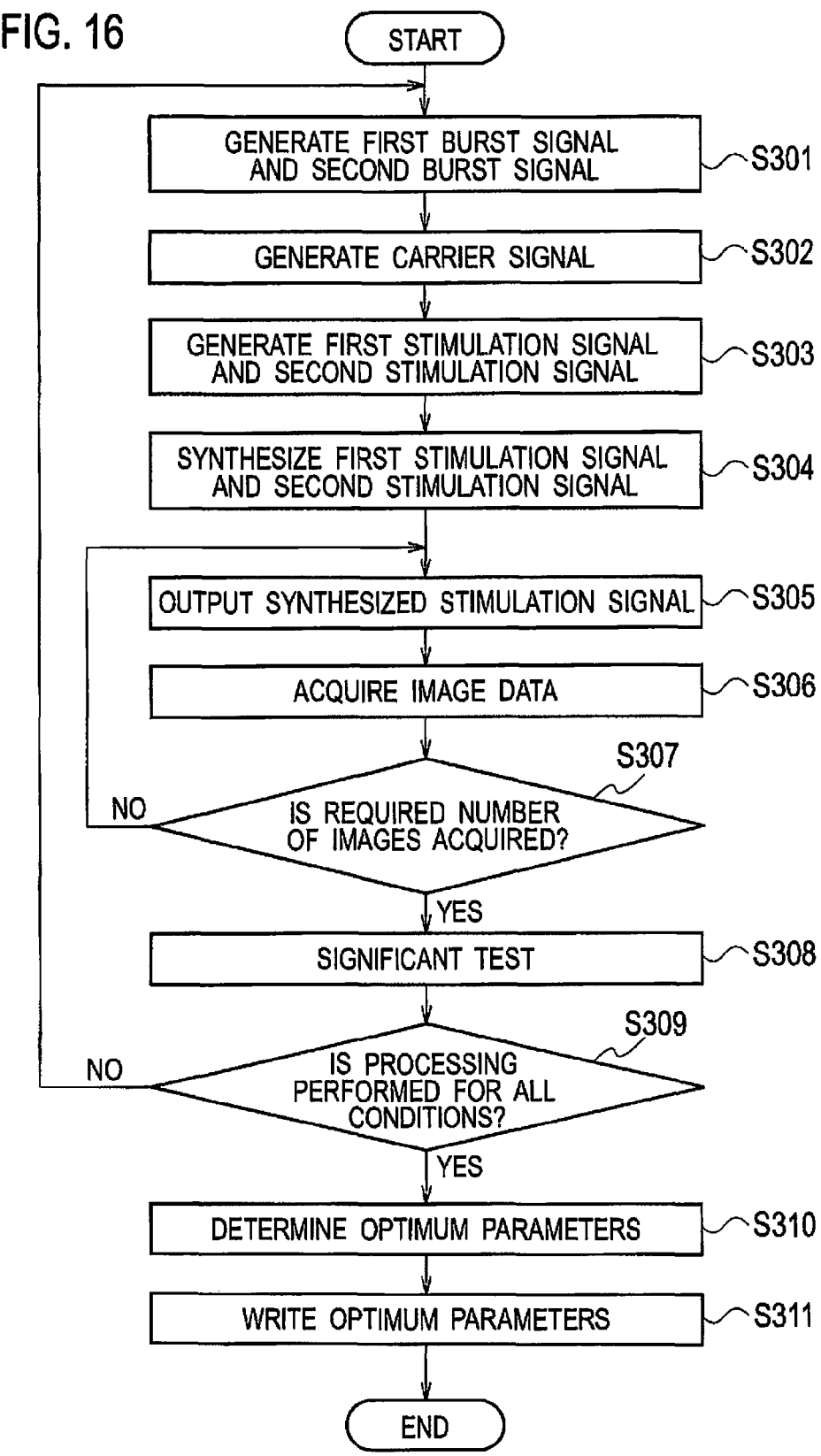
FIG. 16 is a flowchart of assistance in explaining the preprocessing in the stimulation signal generation device of FIG. 12.

Description will be given with reference to a flowchart illustrated in FIG. 16 with regard to the preprocessing which the stimulation signal generation device 1c according to the second embodiment performs before assisting exercise.

First, upon receipt of input of the operation signal to start the preprocessing, the burst signal generator 101a of the stimulation signal generation device 1c extracts the value of the frequency of the first burst signal and the value of the frequency of the second burst signal from the preprocessing data 111c, and generates the first burst signal and the second burst signal according to the extracted values (at step S301). Also, the carrier signal generator 101b extracts the value of the frequency of the carrier signal from the preprocessing data 111c, and generates the carrier signal according to the extracted value (at step S302).

The convolution embedding unit 101c generates the first stimulation signal by superimposing the carrier signal generated at step S302 on the first burst signal generated at step S301, and generates the second stimulation signal by superimposing the carrier signal generated at step S302 on the second burst signal generated at step S301 (at step S303).

After that, the synthesizer 107 generates a new stimulation signal by synthesizing the first stimulation signal and the second stimulation signal generated at step S303, at a ratio specified by the stimulation signal ratio contained in the preprocessing data 111c, and outputs stimulation data by outputting the newly generated stimulation signal in conjunction with the duty ratio (at step S304).

Then, the output unit 102 outputs the stimulation signal generated newly through synthesis at step S303 to the stimulation pads unit 2 according to the duty ratio contained in the stimulation data (at step S305). Thereby, the stimulation pads unit 2 applies stimulation to the user's nerve according to the stimulation signal.

When the output unit 102 outputs the stimulation signal and thereby the stimulation pads unit 2 applies the stimulation to the user, the brain activity data acquisition unit 103 acquires image data captured by the measuring device 3 (at step S306). When the image data is acquired in amounts corresponding to the required number of images for the significant test (YES at step S307), the significant test unit 103b obtains a test result by the significant test (at step S308). Also, when the image data is not acquired in amounts corresponding to the required number of images (NO at step S307), the stimulation signal generation device 1c repeats the processing of steps S305 and S306.

The obtained test result is temporarily stored in the storage device 11 or the memory (unillustrated). When the processing of steps S301 to S308 is performed for all conditions specified by the preprocessing (YES at step S309), the decision unit 104 determines that conditions under which the highest t-value is obtained are optimum parameters, from all values obtained by the significant test unit 103b (at step S310). Also, the decision unit 104 writes the values determined as the optimum parameters, as the parameters for use in the movement assist processing, to the stimulation signal generation program P2 stored in the storage device 11 (at step S311). The parameters include the value of the first burst signal, the value of the second burst signal, the value of the carrier signal, the stimulation signal ratio, and the duty ratio.

Meanwhile, when there is a condition for which the processing is not completed (NO at step S309), the stimulation signal generation device 1c repeats the processing of steps S301 to S308 until test results are obtained for all conditions.

[Assist Processing]

Figure 17:
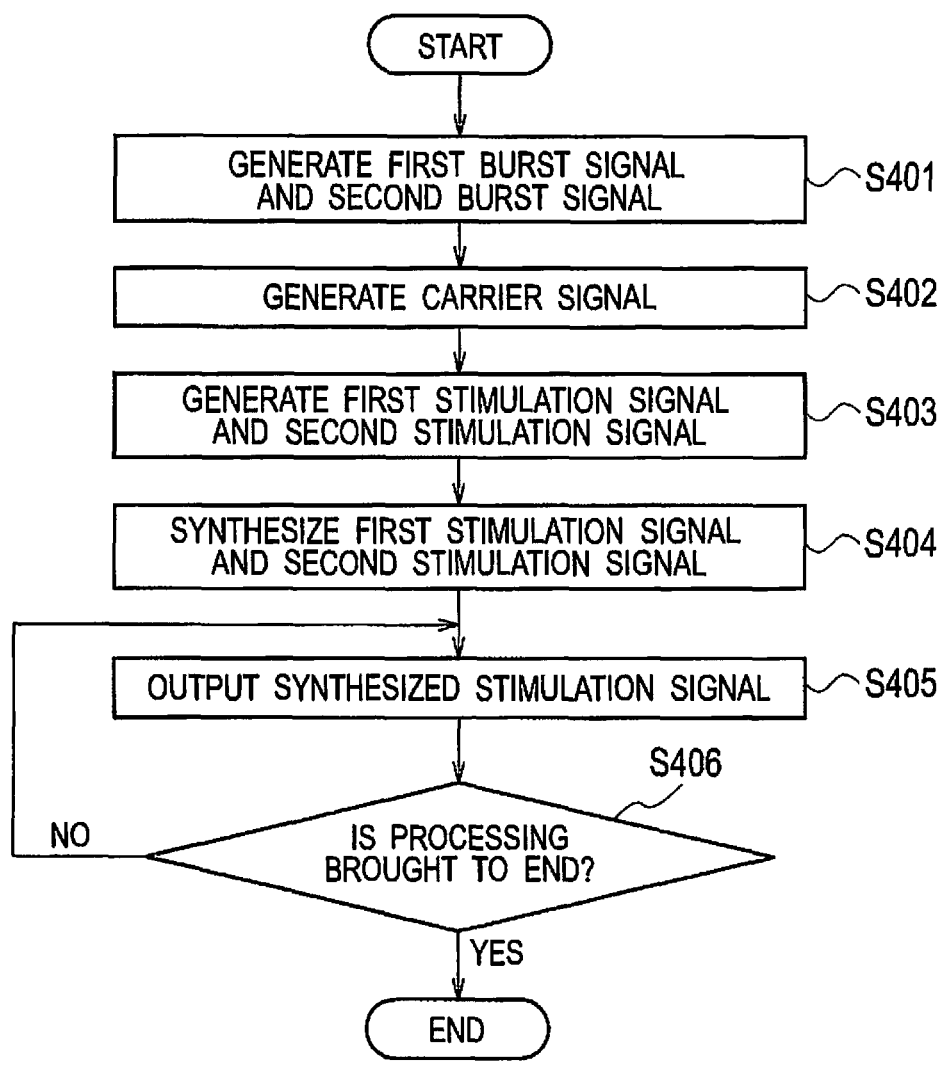
FIG. 17 is a flowchart of assistance in explaining the assist processing in the stimulation signal generation device of FIG. 12.

Next, description will be given with reference to a flowchart illustrated in FIG. 17 with regard to the assist processing for assisting the user's exercise, which the stimulation signal generation device 1c according to the second embodiment performs after having performed the preprocessing to write the optimum conditions (or parameters) to the stimulation signal generation program P2.

In the stimulation signal generation device 1c, upon receipt of input of the operation signal to start the exercise assist, the burst signal generator 101a generates the first burst signal and generates the second burst signal according to the values specified by the stimulation signal generation program P2 (at step S401). Also, the carrier signal generator 101b generates the carrier signal according to the value specified by the stimulation signal generation program P2 (at step S402).

Then, the convolution embedding unit 101c generates the first stimulation signal by superimposing the carrier signal generated at step S402 on the first burst signal generated at step S401, and generates the second stimulation signal by superimposing the carrier signal generated at step S402 on the second burst signal generated at step S401 (at step S403).

After that, the synthesizer 107 generates a new stimulation signal by synthesizing the first stimulation signal and the second stimulation signal generated at step S403, according to the synthetic ratio contained in the stimulation signal generation program P2, and outputs stimulation data by outputting the newly generated stimulation signal in conjunction with the duty ratio (at step S404).

The output unit 102 outputs the stimulation signal generated newly through synthesis at step S404 to the stimulation pads unit 2 according to the duty ratio contained in the stimulation data (at step S405). Thereby, the stimulation pads unit 2 applies stimulation to the user's nerve according to the stimulation signal. Also, the output unit 102 repeats the processing of step S405 until it receives input of the operation signal to end the assist processing (at step S406).

As described above, the stimulation signal generation device 1c assists the user's exercise by using the stimulation signal transmitted through the skin and the muscle to the nerve. Also, for stimulation signal generation, the stimulation signal generation device is uses a frequency suitable for the user and uses a stimulation signal obtained by synthesizing the stimulation signals of plural frequencies. When the stimulation signal generation device 1c is used to assist the exercise, therefore, the user suffers no pain and convulsions and easily perceives stimulation, and the exercise assist effect can also be sustained for long periods.

Also, the stimulation signal generation device 1c applies stimulation for training for the user's somatosensory area or the parietal association area or the prefrontal area around the somatosensory area, and thereby, the activity of the somatosensory area or the parietal association area or the prefrontal area around the somatosensory area becomes active, which in turn makes it easy for the user to do exercise even when stimulation is not applied. Also, the stimulation signal generation device is applies stimulation thereby to enable restrengthening not only the affected side but also the unaffected side.

Also in the stimulation signal generation device 1c, it is most desirable that the preprocessing be performed for each user to determine optimum parameters for use; however, parameters obtained by performing the preprocessing on a certain user may be used for a different user (or a third party) to perform the assist processing. In this case, it is desirable that parameters obtained by performing the preprocessing on a user similar in conditions (e.g. a symptom, a body type, age, sex, etc.) be used for a different user to perform the assist processing.

Incidentally, also in the stimulation signal generation device 1c, when the brain activity can be measured at the same time that the stimulation signal is outputted, the burst signal and the carrier signal may be directly generated without overwriting the stimulation signal generation program P2 with the newly obtained values.

[Third Embodiment]

Figure 18:
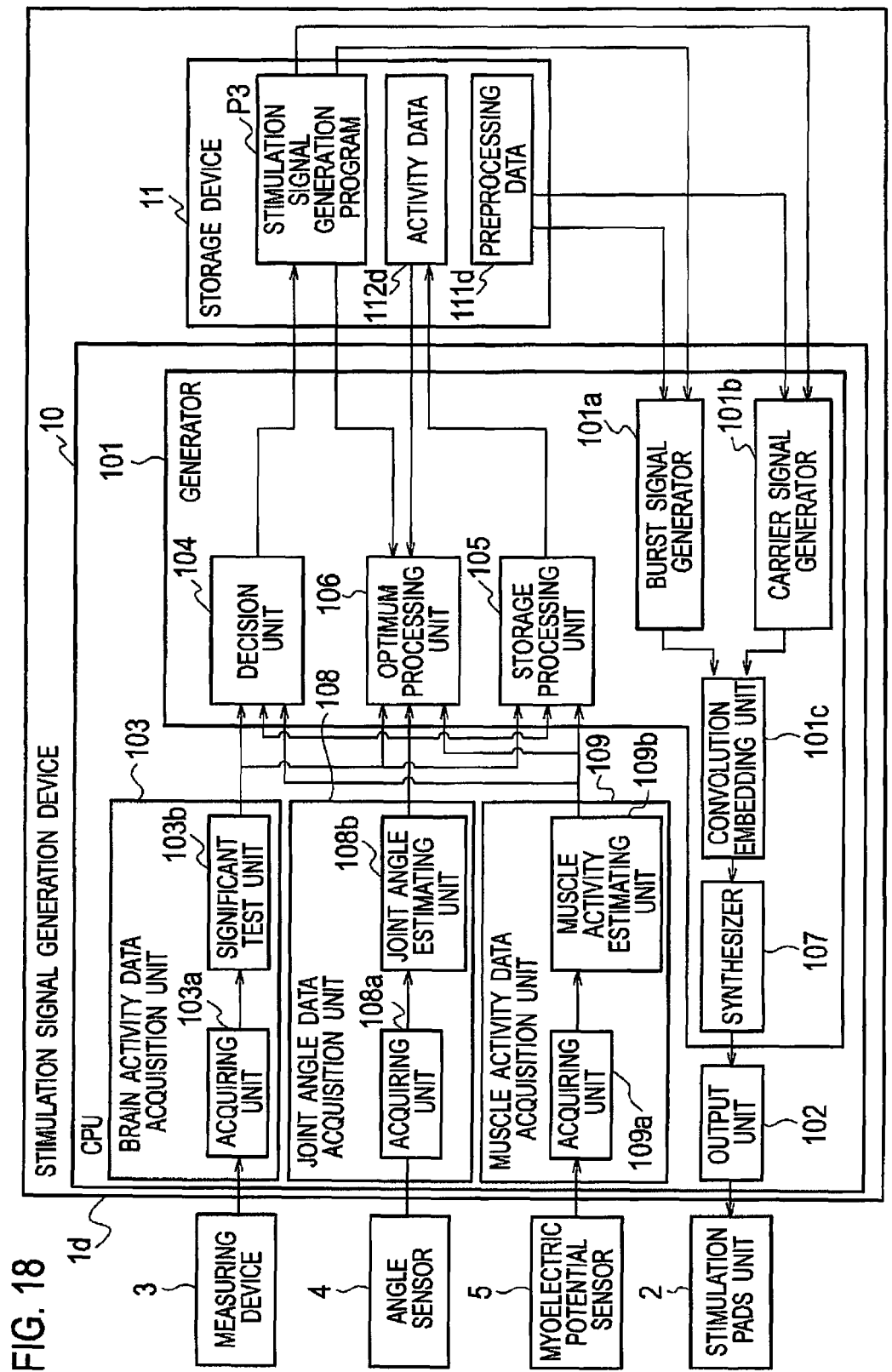
FIG. 18 is a block diagram of assistance in explaining a configuration of a stimulation signal generation device according to a third embodiment.

As illustrated in FIG. 18, a stimulation signal generation device 1d according to a third embodiment of the present invention is different in that the generator 101 includes the storage processing unit 105 and the optimization processing unit 106, the stimulation signal generation device 1d includes a joint angle data acquisition unit 108 and a muscle activity data acquisition unit 109, and the storage device 20 stores activity data 112d, as compared to the stimulation signal generation device is described above with reference to FIG. 12. The stimulation signal generation device 1d is configured so that the generator 101, the output unit 102, the brain activity data acquisition unit 103, the decision unit 104, the storage processing unit 105, the optimization processing unit 106, the synthesizer 107, the joint angle data acquisition unit 108 and the muscle activity data acquisition unit 109 are implemented in the central processing unit (CPU) 10 as illustrated in FIG. 18, by installing a stimulation signal generation program P3 in the information processing apparatus including the CPU 10 and the storage device 11.

The stimulation signal generation device 1d has connections to an angle sensor 4 and a myoelectric potential sensor 5, in addition to the stimulation pads unit 2 and the measuring device 3. The angle sensor 4 is attached to a joint such as a shoulder joint or a hip joint of the user to be assisted in his or her movement by the stimulation signal generation device 1d, and measures an angle such as a bend angle or a stretch angle as movement of the joint, and an angular velocity. Also, the myoelectric potential sensor 5 is attached to the skin in the vicinity of a muscle which the user moves, and measures the myoelectric potential of the muscle from movement of the skin surface.

The stimulation signal generation device 1d uses the activity data 112d generated by using data obtained from the stimulated user, as given below: joint angle data obtained by the joint angle data acquisition unit 108 and muscle activity data obtained by the muscle activity data acquisition unit 109, in addition to brain activity data obtained by the brain activity data acquisition unit 103.

For example, the joint angle data acquisition unit 108 includes an acquiring unit 108a and a joint angle estimating unit 108b. The acquiring unit 108a is connected to the angle sensor 4, and acquires measured results obtained by the angle sensor 4, in accordance with the outputting of the stimulation signal from the output unit 102. The joint angle estimating unit 108b estimates the angle of the user's joint and the angular velocity from the measured results acquired by the acquiring unit 108a, and outputs the estimated angle and angular velocity as angle data.

For example, the muscle activity data acquisition unit 109 includes an acquiring unit 109a and a muscle activity estimating unit 109b. The acquiring unit 109a is connected to the myoelectric potential sensor 5, and acquires measured results obtained by the myoelectric potential sensor 5, in accordance with the outputting of the stimulation signal from the output unit 102. The muscle activity estimating unit 109b estimates the muscle activity of the user from the measured results acquired by the acquiring unit 109a, and outputs the estimated muscle activity as muscle activity data.

When writing the optimum t-value obtained by the preprocessing to the stimulation signal generation program P3, the decision unit 104 of the stimulation signal generation device 1d also writes the estimated angle data and muscle activity data in addition to the result of the significant test.

The storage processing unit 105 puts the outputting of the stimulation signal by the stimulation signal generation device 1d, and a list of histories of the activity of the user or the like by the stimulation signal, into storage. Specifically, processed results obtained by the brain activity data acquisition unit 103, processed results obtained by the joint angle data acquisition unit 108 and processed results obtained by the muscle activity data acquisition unit 109 are inputted to form the activity data 112d, which is then stored in the storage device 11. Here, when the activity data 112d is already stored in the storage device 11, a new value is added to update the activity data 112d.

Upon receipt of new input of a test result obtained by the significant test unit 103b, the angle data outputted by the joint angle estimating unit 108b and the muscle activity data outputted by the muscle activity estimating unit 109b, the optimization processing unit 106 compares the test result with the current significant test result (or t-value) specified by the stimulation signal generation program P3. Also, when the newly inputted t-value is larger than the current t-value, the optimization processing unit 106 updates the stimulation signal generation program P3 with the current conditions and values.

As illustrated for example in Part (b) of FIG. 19, the activity data 112d includes the frequency of the first burst signal, the frequency of the second burst signal, the frequency of the carrier signal, the stimulation signal ratio, and the duty ratio, as the stimulation parameters. Also, the measured results include the angle data and the muscle activity data in addition to the location and the t-value.

[Preprocessing]

Figure 20:
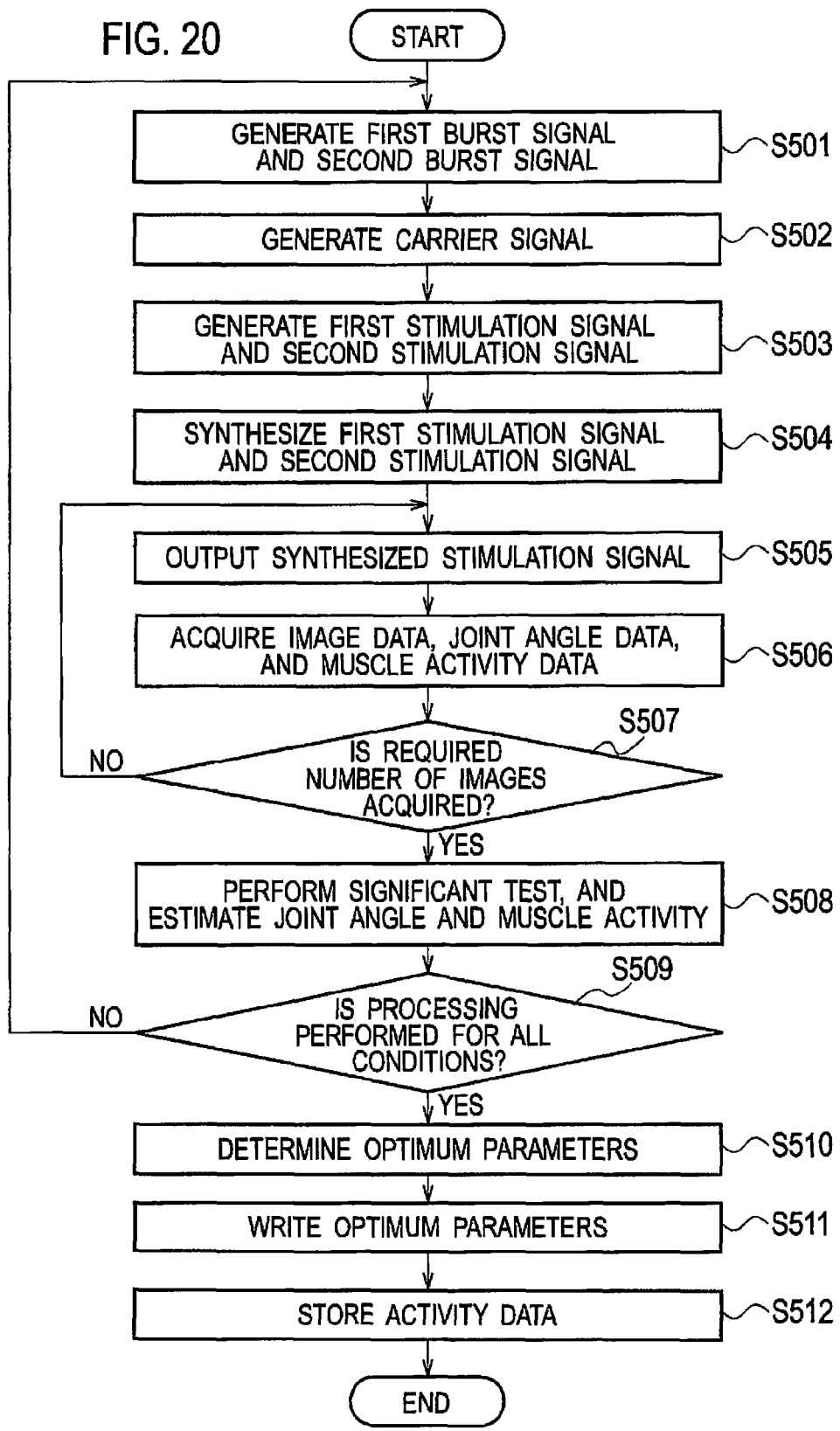
FIG. 20 is a flowchart of assistance in explaining the preprocessing in the stimulation signal generation device of FIG. 18.

Description will be given with reference to a flowchart illustrated in FIG. 20 with regard to the preprocessing which the stimulation signal generation device 1d according to the third embodiment performs before assisting exercise.

First, upon receipt of input of the operation signal to start the preprocessing, the burst signal generator 101a of the stimulation signal generation device 1d extracts the value of the frequency of the first burst signal and the value of the frequency of the second burst signal from preprocessing data 111$d$ as illustrated in Part (a) of FIG. 19, and generates the first burst signal and the second burst signal according to the extracted values (at step S501). Also, the carrier signal generator 101$b$ extracts the value of the frequency of the carrier signal from the preprocessing data 111$d$, and generates the carrier signal according to the extracted value (at step S502).

The convolution embedding unit 101$c$ generates the first stimulation signal by superimposing the carrier signal generated at step S502 on the first burst signal generated at step S501, and generates the second stimulation signal by superimposing the carrier signal generated at step S502 on the second burst signal generated at step S501 (at step S503).

After that, the synthesizer 107 generates a new stimulation signal by synthesizing the first stimulation signal and the second stimulation signal generated at step S503, at a ratio specified by the stimulation signal ratio contained in the preprocessing data 111$c$, and outputs stimulation data by outputting the newly generated stimulation signal in conjunction with the duty ratio (at step S504).

Then, the output unit 102 outputs the stimulation signal generated newly through synthesis at step S504 to the stimulation pads unit 2 according to the duty ratio contained in the stimulation data (at step S505). Thereby, the stimulation pads unit 2 applies stimulation to the user's nerve according to the stimulation signal.

When the output unit 102 outputs the stimulation signal and thereby the stimulation pads unit 2 applies the stimulation to the user, the brain activity data acquisition unit 103 acquires image data captured by the measuring device 3, the acquiring unit 108$a$ acquires the joint angle data measured by the angle sensor 4, and the acquiring unit 109$a$ acquires the muscle activity data measured by the myoelectric potential sensor 5 (at step S506). When the image data is acquired in amounts corresponding to the required number of images for the significant test (YES at step S507), the significant test unit 103$b$ obtains a test result by the significant test, the joint angle estimating unit 108$b$ estimates the angle data, and the muscle activity estimating unit 109$b$ estimates the muscle activity data (at step S508). Also, when the image data is not acquired in amounts corresponding to the required number of images (NO at step S507), the stimulation signal generation device 1$d$ repeats the processing of steps S505 and S506.

The test result and estimated results obtained at step S508 are temporarily stored in the storage device 11 or the memory (unillustrated). When the processing of steps S501 to S508 is performed for all conditions specified by the preprocessing (YES at step S509), the decision unit 104 determines the values of optimum stimulation parameters by using all test results obtained by the significant test unit 103$b$, the angle data estimated by the joint angle estimating unit 108$b$, and the muscle activity data estimated by the muscle activity estimating unit 109$b$ (at step S510). After that, the decision unit 104 writes the values determined as the optimum stimulation parameters, to the stimulation signal generation program P3 (at step S511).

Also, the storage processing unit 105 generates the activity data 112$c$ and stores the activity data 112$d$ in the storage device 11 (at step S512), and the preprocessing comes to an end. Meanwhile, when there is a condition for which the processing is not completed (NO at step S509), the stimulation signal generation device 1$d$ repeats the processing of steps S501 to S508 until test results are obtained for all conditions.

[Assist Processing]

Figure 21:
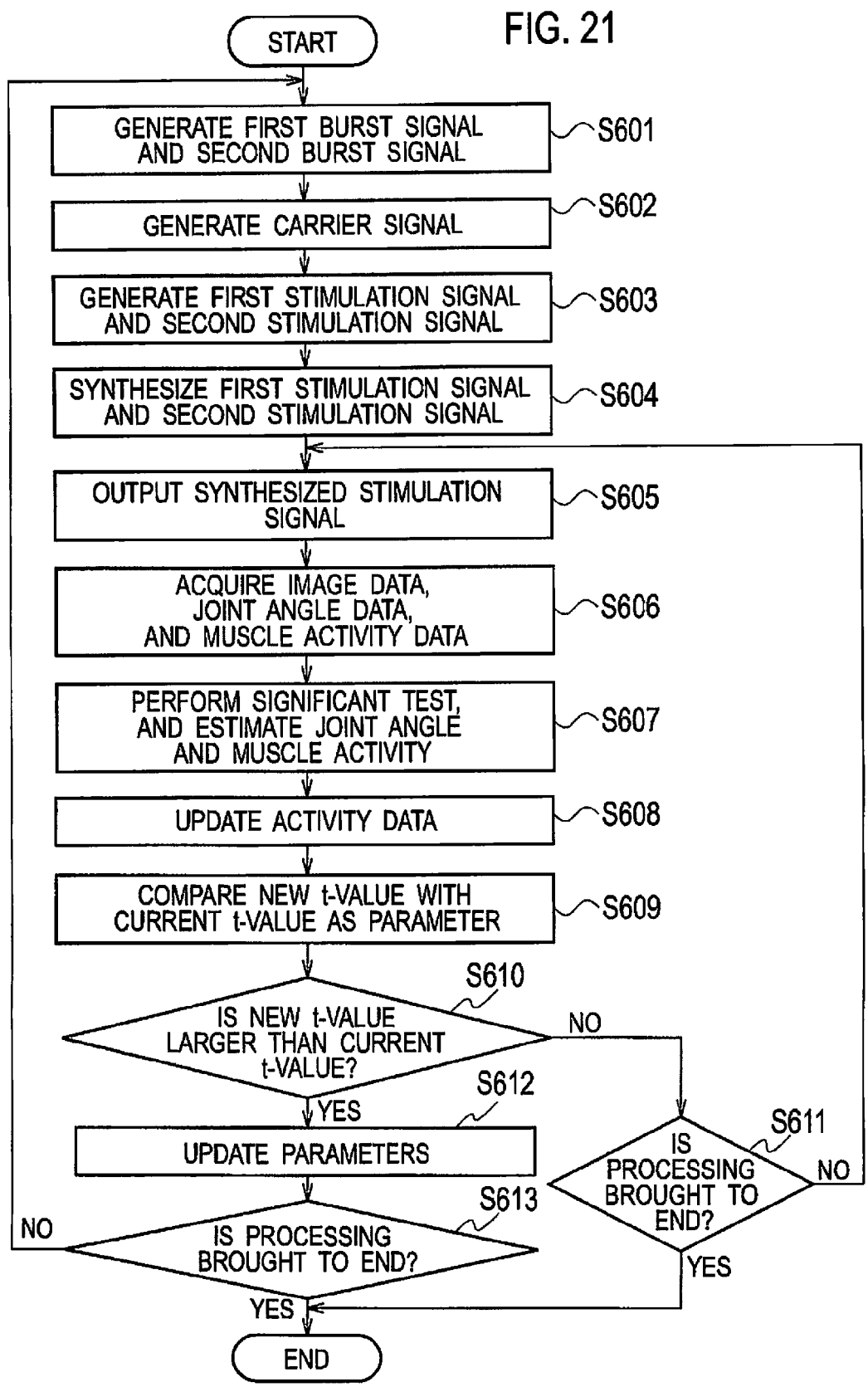
FIG. 21 is a flowchart of assistance in explaining the assist processing in the stimulation signal generation device of FIG. 18.

Next, description will be given with reference to a flowchart illustrated in FIG. 21 with regard to the assist processing for assisting the user's exercise, which the stimulation signal generation device 1$d$ according to the third embodiment performs after having performed the preprocessing to write the optimum conditions (or parameters) to the stimulation signal generation program P3. Incidentally, in the case of the preprocessing, the measuring device 3 connected to the stimulation signal generation device 1$d$ may be the MRI apparatus; however, in the case of the assist processing, the measuring device 3 is described as being the device capable of measuring the brain activity while the user is doing exercise, such as the electroencephalograph or the near-infrared optical imaging devices, rather than the MRI apparatus.

In the stimulation signal generation device 1$d$, upon receipt of input of the operation signal to start the exercise assist, the burst signal generator 101$a$ generates the first burst signal and generates the second burst signal according to the values specified by the stimulation signal generation program P3 (at step S601). Also, the carrier signal generator 101$b$ generates the carrier signal according to the value specified by the stimulation signal generation program P3 (at step S602).

Then, the convolution embedding unit 101$c$ generates the first stimulation signal by superimposing the carrier signal generated at step S602 on the first burst signal generated at step S601, and generates the second stimulation signal by superimposing the carrier signal generated at step S602 on the second burst signal generated at step S601 (at step S603).

After that, the synthesizer 107 generates a new stimulation signal by synthesizing the first stimulation signal and the second stimulation signal generated at step S603, according to the synthetic ratio contained in the activity data 112$d$, and outputs stimulation data by outputting the newly generated stimulation signal in conjunction with the duty ratio (at step S604).

The output unit 102 outputs the stimulation signal generated newly through synthesis at step S604 to the stimulation pads unit 2 according to the duty ratio contained in the stimulation data (at step S605). Thereby, the stimulation pads unit 2 applies stimulation to the user's nerve according to the stimulation signal. When the stimulation is applied to the user, the brain activity data acquisition unit 103 acquires image data captured by the measuring device 3, the joint angle data acquisition unit 108 acquires the joint angle data measured by the angle sensor 4, and the muscle activity data acquisition unit 109 acquires the muscle activity data measured by the myoelectric potential sensor 5 (at step S606). Also, the significant test unit 103$b$ performs the significant test, the joint angle estimating unit 108$b$ estimates the joint angle data, and the muscle activity estimating unit 109$b$ estimates the muscle activity data (at step S607).

The storage processing unit 105 updates the activity data 112$d$ stored in the storage device 11, by adding a newly obtained result of the significant test, the joint angle data, the muscle activity data, and parameters under which these values are obtained (at step S608).

Also, the optimization processing unit 106 performs a comparison between the t-value as the parameter being used in the stimulation signal generation program P3 and the t-value obtained newly by the significant test (at step S609). When the result of the comparison performed at step S609 shows that the newly obtained t-value is smaller than the t-value as the parameter being used in the stimulation signal generation program P3 (NO at step S610), the processing returns to step S605 if the assist processing is not brought to an end (NO at step S611).

Meanwhile, when the result of the comparison performed at step S609 shows that the newly obtained t-value is larger than the t-value as the parameters being currently used in the stimulation signal generation program P3 (YES at step S610), the values in the stimulation signal generation program P3 are overwritten with the newly obtained t-value and the values of parameters under which the t-value is obtained (at step S612). After that, if the assist processing is not brought to an end, the processing returns to step S601 (NO at step S613).

Incidentally, also in the stimulation signal generation device 1d, after the synthesizer 107 has synthesized the first burst signal and the second burst signal, the convolution embedding unit 101c may superimpose the carrier signal on the synthesized burst signal. Alternatively, the stimulation signal generation device 1d may also use the first burst signal as the first stimulation signal and use the second burst signal as the second stimulation signal without the use of the carrier signal. Further, also in the stimulation signal generation device 1d, when the brain activity can be measured at the same time that the stimulation signal is outputted, the burst signal and the carrier signal may be directly generated without overwriting the stimulation signal generation program P3 with the newly obtained values.

As described above, the stimulation signal generation device 1d assists the user's exercise by using the stimulation signal transmitted through the skin and the muscle to the nerve. Also, for stimulation signal generation, the stimulation signal generation device 1d uses a frequency suitable for the user and uses a stimulation signal obtained by synthesizing the stimulation signals of plural frequencies. When the stimulation signal generation device 1d is used to assist the exercise, therefore, the user suffers no pain and convulsions and easily perceives stimulation, and the exercise assist effect can also be sustained for long periods.

Also, the stimulation signal generation device 1d applies stimulation for training for the user's somatosensory area or the parietal association area or the prefrontal area around the somatosensory area, and thereby, the activity of the somatosensory area or the parietal association area or the prefrontal area around the somatosensory area becomes active, which in turn makes it easy for the user to do exercise even when stimulation is not applied. Also, the stimulation signal generation device 1d applies stimulation thereby to enable restrengthening not only the affected side but also the unaffected side.

Incidentally, also in the stimulation signal generation device 1d, it is most desirable that the preprocessing be performed for each user to determine optimum parameters for use; however, parameters obtained by performing the preprocessing on a certain user may be used for a different user (or a third party) to perform the assist processing. In this case, it is desirable that parameters obtained by performing the preprocessing on a user similar in conditions (e.g. a symptom, a body type, age, sex, etc.) be used for a different user to perform the assist processing.

EXAMPLE 1

An Example of Assistive Walking and Functional Recovery of an Individual with Hemiplegic Paralysis during Acute Phase Description will be given below with regard to Example in which the stimulation signal generation device 1c according to the embodiment is used to assist walking. Example 1 uses a stimulation signal formed by mixing the first burst signal and the second burst signal, the first burst signal has a frequency of 50 Hz and the second burst signal has a frequency of 100 Hz, and the ratio of the first burst signal to the second burst signal is seven to three.

The user is a female in her sixties who has developed symptoms of left hemiplegia and articulation disorder caused by progressive cerebral infarction. In the onset of the symptoms, clinical evaluations of the user indicated a Brunnstrome recovery stage (BRS) III and a Berg balance scale (BBS) of 6, and she was able to maintain a seated position on her own, required assistance to stand, and walked with assistance (97.7 seconds/10 m). When the stimulation signal generation device 1b was used to start applying electrical stimulation on the 10th day after the development of the symptoms, which had shown no improvement, the user's walking speed was improved twofold on the same day, and she walked with assistance (48.6 seconds/10 m). Also, when rehabilitation was continued using electrical stimulation by the stimulation signal generation device 1c, the user's recovery was rated a BRS V on the 19th day after the development of the symptoms, and her BBS score was improved to 35 points and she had been able to begin walking with a T-crutch (19 seconds/10 m) on the 21th day after the development of the symptoms.

EXAMPLE 2

An Example of Assistive Walking and Functional Recovery of an Individual with Hemiplegic Paralysis During Convalescent Phase Description will be given with regard to another Example in which the stimulation signal generation device 1c according to the embodiment is used to assist walking. Example 2 also uses the stimulation signal formed by mixing the first burst signal and the second burst signal, the first burst signal has a frequency of 50 Hz and the second burst signal has a frequency of 100 Hz, and the ratio of the first burst signal to the second burst signal is seven to three.

The user is a male in his sixties who has developed symptoms of right hemiplegia and articulation disorder caused by cerebral infarction. On the 36th day after the development of the symptoms, clinical evaluations of the user indicated a leg BRS III, he had no range-of-joint-motion restrictions and T-crutch walking was possible with minimal assistance, but tactile and positional senses were slightly impaired, and the strength of muscle contraction was falling. When the user underwent normal rehabilitation for one week since the 36th day after the development of the symptoms, he recovered and walked with assistance (54 seconds/10 m). Thereafter, rehabilitation was carried out for one week by using the stimulation signal generation device 1c to apply electrical stimulation. As a result, the dorsal flexion angle of his leg joint was improved from −15 degrees to 0 degree, his walking speed was improved twofold, T-crutch walking (22 seconds/10 m) was achieved, and his walking gait was also stabilized.

EXAMPLE 3

An Example of Assistive Finger Motion and Functional Recovery of an Individual with Paralysis During Chronic Phase Description will be given with regard to another Example in which the stimulation signal generation device 1a according to the embodiment is used for purposes of functional recovery of opening and closing motion of fingers of a paralyzed hand. The user is a male in his fifties who had developed symptoms of left paresis with thalamic pain, caused by cerebral stroke, for six years before rehabilitation began. The user was unable to open and close his fingers on the left side for six years and was chronically paralyzed. The user underwent rehabilitation using the stimulation signal generation device 1a using stimulation parameters given below: a stimulation voltage of 14.7 V, a carrier frequency of 2 kHz, a burst frequency of 100 Hz, and a duty ratio of 50%. Also, in this rehabilitation, the stimulation pads units 2 were attached directly on the user's extensor pollicis longus muscle, extensor carpi radialis longus muscle, extensor carpi ulnaris muscle and extensor digitorum communis muscle.

The rehabilitation was carried out by checking whether or not voluntary motion was possible after training. The training was conducted in the following manner: the user switched on and off the stimulation signal generation device 1a on the healthy side and simultaneously opened and closed the paralyzed hand. The user underwent the training ten times for about two minutes. As a result, it was observed that, immediately after the completion of the training, the user was able to continue voluntarily opening and closing his fingers ten or more times without the use of electrical stimulation. Also, it was observed that this effect persisted for two days.

EXAMPLE 4

An Example of Assistive Foot Joint Motion and Functional Recovery of an Individual with Paralysis During Chronic Phase The same user as Example 3 underwent rehabilitation for foot joint motion, using the stimulation signal generation device 1a using the same stimulation parameters.

In the rehabilitation, the stimulation pads unit 2 was attached directly on the user's tibialis anterior muscle to apply electrical stimulation and thereby assist the dorsal flexion of the foot joint. Also, a goniometer was attached to the user's foot joint to measure the angle of rotation of the foot joint for purposes of quantitative observation of the state of functional recovery. Before the rehabilitation began, the maximum dorsal flexion angle of the user's foot joint in the range of joint motion had been 40 degrees, which had been measured in passive exercise by a physiotherapist.

This experiment was divided into the following five stages a) to e), and the angle of rotation of the foot joint was obtained in each stage.

a) Voluntary motion without electrical stimulation: the angle of rotation was 0 degree.

b) Electrical stimulation only: the angle of rotation was 34 degrees, and the assistive motion was 85%.

c) Voluntary motion without electrical stimulation: the angle of rotation was 0 degree.

d) Voluntary motion with electrical stimulation: the angle of rotation was 30 degrees, and the assistive motion was 75%.

e) Voluntary motion without electrical stimulation: the angle of rotation was 5 degrees, and the recovery was 12%.

At first, the user could not move his foot joint at all with the voluntary motions a) and c); however, immediately after a session of training d) which involved carrying out both the electrical stimulation and the voluntary motion simultaneously, the user was able to achieve the dorsal flexion of his foot joint five times by the voluntary motion, and it was observed that the functional recovery was 12%. This effect persisted for about two days after the rehabilitation.

REFERENCE SIGNS LIST 1a-1d stimulation signal generation devices
10 central processing unit
101 generator
101a burst signal generator
101b carrier signal generator
101c convolution embedding unit
102 output unit
103 brain activity data acquisition unit
103a acquiring unit
103b significant test unit
104 decision unit
105 storage processing unit
106 optimization processing unit
107 synthesizer
108 joint angle data acquisition unit
108a acquiring unit
108b joint angle estimating unit
109 muscle activity data acquisition unit
109a acquiring unit
109b muscle activity estimating unit
11 storage device
111a-111c activity data
2 stimulation pads unit
3 measuring device
4 angle sensor
5 myoelectric potential sensor

The invention claimed is:

1. A stimulation signal generation device for generating a stimulation signal to be used to assist exercise of a human body, comprising:
   a generator configured to, during preprocessing, generate a stimulation signal based on preprocessing stimulation parameters predetermined for the preprocessing, the stimulation signal to be applied to both an afferent neuron and an efferent neuron of nerve of the human body, corresponding to a specific brain region to be activated in order to move a joint of the human body, and configured to, during assist processing, generate the stimulation signal to be applied for the activity of the specific brain region, based on assist-processing stimulation parameters inputted to the generator;
   an output unit configured to output the stimulation signal generated by the generator, to stimulation pads attached in the vicinity of the joint of the human body and configured to apply stimulation through the skin to both the afferent neuron and the efferent neuron;
   a brain activity data acquisition unit configured to acquire data on activity of a brain under application of the stimulation by the stimulation signal outputted by the output unit; and
   a decision unit configured to obtain a set of optimum stimulation parameters from the data acquired by the brain activity data acquisition unit, to use the set of optimum stimulation parameters as the assist-processing stimulation parameters, and to output the set of optimum stimulation parameters to the generator.

2. The stimulation signal generation device according to claim 1, wherein
   the brain activity data acquisition unit obtains a value indicating the brain activity by performing a significant amount of testing, and
   the decision unit determines a set of optimum stimulation parameters, as the preprocessing stimulation parameters that maximizes the value obtained by the brain activity data acquisition unit.

3. The stimulation signal generation device according to claim 2, wherein the stimulation parameters include a frequency of the stimulation signal.

4. The stimulation signal generation device according to claim 3, wherein
the stimulation parameters include a plurality of frequencies, and a synthetic ratio between stimulation signals of the plurality of frequencies,
the stimulation signal generation device further comprises a synthesizer configured to, when the generator generates the stimulation signals of the plurality of frequencies included in the stimulation parameters, form a stimulation signal by synthesizing the stimulation signals of the plurality of frequencies at the synthetic ratio included in the stimulation parameters, and
the output unit outputs the stimulation signal synthesized by the synthesizer, when the plurality of frequencies are included in the stimulation parameters.

5. The stimulation signal generation device according to claim 4, wherein
the stimulation parameters include a frequency value of a burst signal to determine the stimulation signal to be applied to the nerve, and a frequency value of a carrier signal to determine a rectangular wave of a frequency which is higher than the frequency of the burst signal and passes through the skin, the frequency value of the burst signal and the frequency value of the carrier signal being related to each other, and
the generator includes a convolution embedding unit for forming a stimulation signal to convolve the burst signal and the carrier signal generated by using the frequency values included in the stimulation parameters.

6. The stimulation signal generation device according to claim 3, wherein
the stimulation parameters include a plurality of frequencies, and a synthetic ratio between stimulation signals of the plurality of frequencies,
the stimulation signal generation device further comprises a synthesizer configured to, when the generator generates the stimulation signals of the plurality of frequencies included in the stimulation parameters, form a stimulation signal by synthesizing the stimulation signals of the plurality of frequencies at the synthetic ratio included in the stimulation parameters,
the output unit outputs the stimulation signal synthesized by the synthesizer, when the plurality of frequencies are included in the stimulation parameters, and
the decision unit determines the synthetic ratio included in the stimulation parameters, from the data on the brain activity acquired by the brain activity data acquisition unit.

7. The stimulation signal generation device according to claim 3, wherein
the stimulation parameters include a frequency value of a burst signal to determine the stimulation signal to be applied to the nerve, and a frequency value of a carrier signal to determine a rectangular wave of a frequency which is higher than the frequency of the burst signal and passes through the skin, the frequency value of the burst signal and the frequency value of the carrier signal being related to each other, and
the generator includes a convolution embedding unit for forming a stimulation signal to convolve the burst signal and the carrier signal generated by using the frequency values included in the stimulation parameters.

8. The stimulation signal generation device according to claim 6, wherein
the stimulation parameters include a frequency value of a burst signal to determine the stimulation signal to be applied to the nerve, and a frequency value of a carrier signal to determine a rectangular wave of a frequency which is higher than the frequency of the burst signal and passes through the skin, the frequency value of the burst signal and the frequency value of the carrier signal being related to each other, and
the generator is embedded a convolution method for forming a stimulation signal to convolve the burst signal and the carrier signal generated by using the frequency values included in the stimulation parameters.

9. The stimulation signal generation device according to claim 2, further comprising:
a joint angle data acquisition unit configured to acquire angle data including a bend angle or a stretch angle and an angular velocity of a hip joint or a shoulder joint of the human body measured by an angle sensor, wherein
the decision unit determines, as a set of optimum stimulation parameters, the stimulation parameters that make a value acquired by the joint angle data acquisition unit satisfy a predetermined condition and maximizes the value obtained by the brain activity data acquisition unit.

10. The stimulation signal generation device according to claim 9, further comprising:
a muscle activity data acquisition unit configured to acquire muscle activity data on muscle activity in the vicinity of the joint of the human body measured by a myoelectric potential sensor, wherein
the decision unit determines, as a set of optimum stimulation parameters, the stimulation parameters that make a value obtained by the muscle activity data acquisition unit satisfy a predetermined condition and maximizes the value obtained by the brain activity data acquisition unit.

11. The stimulation signal generation device according to claim 2, further comprising:
a muscle activity data acquisition unit configured to acquire muscle activity data on muscle activity in the vicinity of the joint of the human body measured by a myoelectric potential sensor, wherein
the decision unit determines, as a set of optimum stimulation parameters, the stimulation parameters that make a value obtained by the muscle activity data acquisition unit satisfy a predetermined condition and maximizes the value obtained by the brain activity data acquisition unit.

12. The stimulation signal generation device according to claim 1, wherein the stimulation parameters include a frequency of the stimulation signal.

13. The stimulation signal generation device according to claim 12, wherein
the stimulation parameters include a plurality of frequencies, and a synthetic ratio between stimulation signals of the plurality of frequencies,
the stimulation signal generation device further comprises a synthesizer configured to, when the generator generates the stimulation signals of the plurality of frequencies included in the stimulation parameters, form a stimulation signal by synthesizing the stimulation signals of the plurality of frequencies at the synthetic ratio included in the stimulation parameters, and
the output unit outputs the stimulation signal synthesized by the synthesizer, when the plurality of frequencies are included in the stimulation parameters.

14. The stimulation signal generation device according to claim 13, wherein
the stimulation parameters include a frequency value of a burst signal to determine the stimulation signal to be applied to the nerve, and a frequency value of a carrier signal to determine a rectangular wave of a frequency which is higher than the frequency of the burst signal and passes through the skin, the frequency value of the burst signal and the frequency value of the carrier signal being related to each other, and the generator includes a convolution embedding unit for forming a stimulation signal to convolve the burst signal and the carrier signal generated by using the frequency values included in the stimulation parameters.

15. The stimulation signal generation device according to claim 12, wherein the stimulation parameters include a plurality of frequencies, and a synthetic ratio between stimulation signals of the plurality of frequencies, the stimulation signal generation device further comprises a synthesizer configured to, when the generator generates the stimulation signals of the plurality of frequencies in the stimulation parameters, form a stimulation signal by synthesizing the stimulation signals of the plurality of frequencies at the synthetic ratio included in the stimulation parameters, the output unit outputs the stimulation signal synthesized by the synthesizer, when the plurality of frequencies are included in the stimulation parameters, and the decision unit determines the synthetic ratio included in the stimulation parameters, from the data on the brain activity acquired by the brain activity data acquisition unit.

16. The stimulation signal generation device according to claim 15, wherein the stimulation parameters include a frequency value of a burst signal to determine the stimulation signal to be applied to the nerve, and a frequency value of a carrier signal to determine a rectangular wave of a frequency which is higher than the frequency of the burst signal and passes through the skin, the frequency value of the burst signal and the frequency value of the carrier signal being related to each other, and the generator includes a convolution embedding unit for forming a stimulation signal to convolve the burst signal and the carrier signal generated by using the frequency values included in the stimulation parameters.

17. The stimulation signal generation device according to claim 12, wherein the stimulation parameters include a frequency value of a burst signal to determine the stimulation signal to be applied to the nerve, and a frequency value of a carrier signal to determine a rectangular wave of a frequency which is higher than the frequency of the burst signal and passes through the skin, the frequency value of the burst signal and the frequency value of the carrier signal being related to each other, and the generator includes a convolution embedding unit for forming a stimulation signal to convolve the burst signal and the carrier signal generated by using the frequency values included in the stimulation parameters.

18. The stimulation signal generation device according to claim 1, further comprising:

a joint angle data acquisition unit configured to acquire angle data including a bend angle or a stretch angle and an angular velocity of a hip joint or a shoulder joint of the human body measured by an angle sensor, wherein the decision unit determines, as a set of optimum stimulation parameters, the stimulation parameters that make a value acquired by the joint angle data acquisition unit satisfy a predetermined condition and maximizes the value obtained by the brain activity data acquisition unit.

19. The stimulation signal generation device according to claim 18, further comprising:

a muscle activity data acquisition unit configured to acquire muscle activity data on muscle activity in the vicinity of the joint of the human body measured by a myoelectric potential sensor, wherein the decision unit determines, as a set of optimum stimulation parameters, the stimulation parameters that make a value obtained by the muscle activity data acquisition unit satisfy a predetermined condition and maximizes the value obtained by the brain activity data acquisition unit.

20. The stimulation signal generation device according to claim 1, further comprising:

a muscle activity data acquisition unit configured to acquire muscle activity data on muscle activity in the vicinity of the joint of the human body measured by a myoelectric potential sensor, wherein the decision unit determines, as a set of optimum stimulation parameters, the stimulation parameters that make a value obtained by the muscle activity data acquisition unit satisfy a predetermined condition and maximizes the value obtained by the brain activity data acquisition unit.

21. A stimulation signal generation method comprising the steps of:

generating a stimulation signal according to a stimulation parameter determined as a condition for the stimulation signal to be applied to a nerve corresponding to a specific brain region to be activated in order to move a joint of a human body;

outputting the generated stimulation signal;

generating the stimulation signal according to preprocessing stimulation parameters stored in a preprocessing data storage unit which stores the preprocessing stimulation parameters as the condition for the stimulation signal to be applied to the nerve of the human body;

acquiring data on brain activity under application of the stimulation signal to the nerve of the human body according to the preprocessing stimulation parameters;

obtaining a set of optimum stimulation parameters from the acquired data, and applying the set of optimum stimulation parameters for generation of the stimulation signal.

* * * * *